US012733853B2

(12) United States Patent
Karsikas et al.

(10) Patent No.: US 12,733,853 B2
(45) Date of Patent: Sep. 15, 2026

(54) TECHNIQUES FOR MEASURING CUMULATIVE STRESS USING WEARABLE-BASED DATA

(71) Applicant: Oura Health Oy, Oulu (FI)

(72) Inventors: Mari Paulina Karsikas, Oulu (FI); Anu Minna Kaarina Pramila, Oulu (FI); Emmi Maria Johanna Antikainen, Pirkkala (FI); Anna Iashina, Tampere (FI)

(73) Assignee: Oura Health Oy, Oulu (FI)

( * ) Notice: Subject to any disclaimer, the term of this patent is extended or adjusted under 35 U.S.C. 154(b) by 301 days.

(21) Appl. No.: 18/452,942

(22) Filed: Aug. 21, 2023

(65) Prior Publication Data

US 2025/0064367 A1 Feb. 27, 2025

(51) Int. Cl.

*A61B 5/16* (2006.01)
*A61B 5/00* (2006.01)
*A61B 5/024* (2006.01)

(52) U.S. Cl.

CPC .......... *A61B 5/165* (2013.01); *A61B 5/02405* (2013.01); *A61B 5/02438* (2013.01); *A61B 5/7275* (2013.01); *A61B 5/6826* (2013.01); *A61B 5/7475* (2013.01)

(58) Field of Classification Search

CPC ................ A61B 5/165; A61B 5/02405; A61B 5/02438; A61B 5/7275; A61B 5/6826; A61B 5/7475; A61B 5/681

See application file for complete search history.

(56) References Cited

U.S. PATENT DOCUMENTS 10,582,862 B1 * 3/2020 Selvaraj .................. A61B 5/11
2007/0260147 A1 * 11/2007 Giftakis ................ A61B 5/349 600/483
2015/0238140 A1 * 8/2015 LaBelle ............ A61B 5/02405 600/300
2015/0305675 A1 * 10/2015 Miller ................... A61B 5/165 600/301
2016/0027324 A1 * 1/2016 Wisbey ................. G16H 40/63 434/247
2017/0132946 A1 * 5/2017 Kinnunen ............. A61B 5/165
2018/0310867 A1 * 11/2018 Sivan .................... A61B 5/165
2023/0114135 A1 * 4/2023 Wiggermann ......... G16H 40/20 705/7.42

* cited by examiner

*Primary Examiner* — Sana Sahand

(74) *Attorney, Agent, or Firm* — ArentFox Schiff LLP

(57) ABSTRACT

Methods, systems, and devices for measuring cumulative stress of a user are described. A system may determine a first and second baseline heart rate variability (HRV) values of the user during periods that the user is awake and asleep, respectively. The system may then acquire physiological data from the user throughout a time interval, and determine a first set of HRV values during periods that the user is awake, and a second set of HRV values during periods that the user is asleep. The system may then determine a cumulative stress level of the user based on comparisons between the first set of HRV values and the first baseline HRV value, and between the second set of HRV values and the second baseline HRV value, where the cumulative stress level is associated with a total amount and/or trend of the user's stress level experienced throughout the time interval.

19 Claims, 13 Drawing Sheets

Resilience to Stress Evaluation

TECHNIQUES FOR MEASURING CUMULATIVE STRESS USING WEARABLE-BASED DATA

FIELD OF TECHNOLOGY

The following relates to wearable devices and data processing, including techniques for measuring cumulative stress using wearable-based data.

BACKGROUND

Some wearable devices may be configured to collect data from users associated with heart rate, motion data, temperature data, photoplethysmogram (PPG) data, and the like. In some cases, some wearable devices may perform various actions, such as providing certain health insights to users based on acquired physiological data in order to assist the user with improving their overall health. However, conventional techniques implemented by wearable devices are deficient.

DETAILED DESCRIPTION

Figure 1:
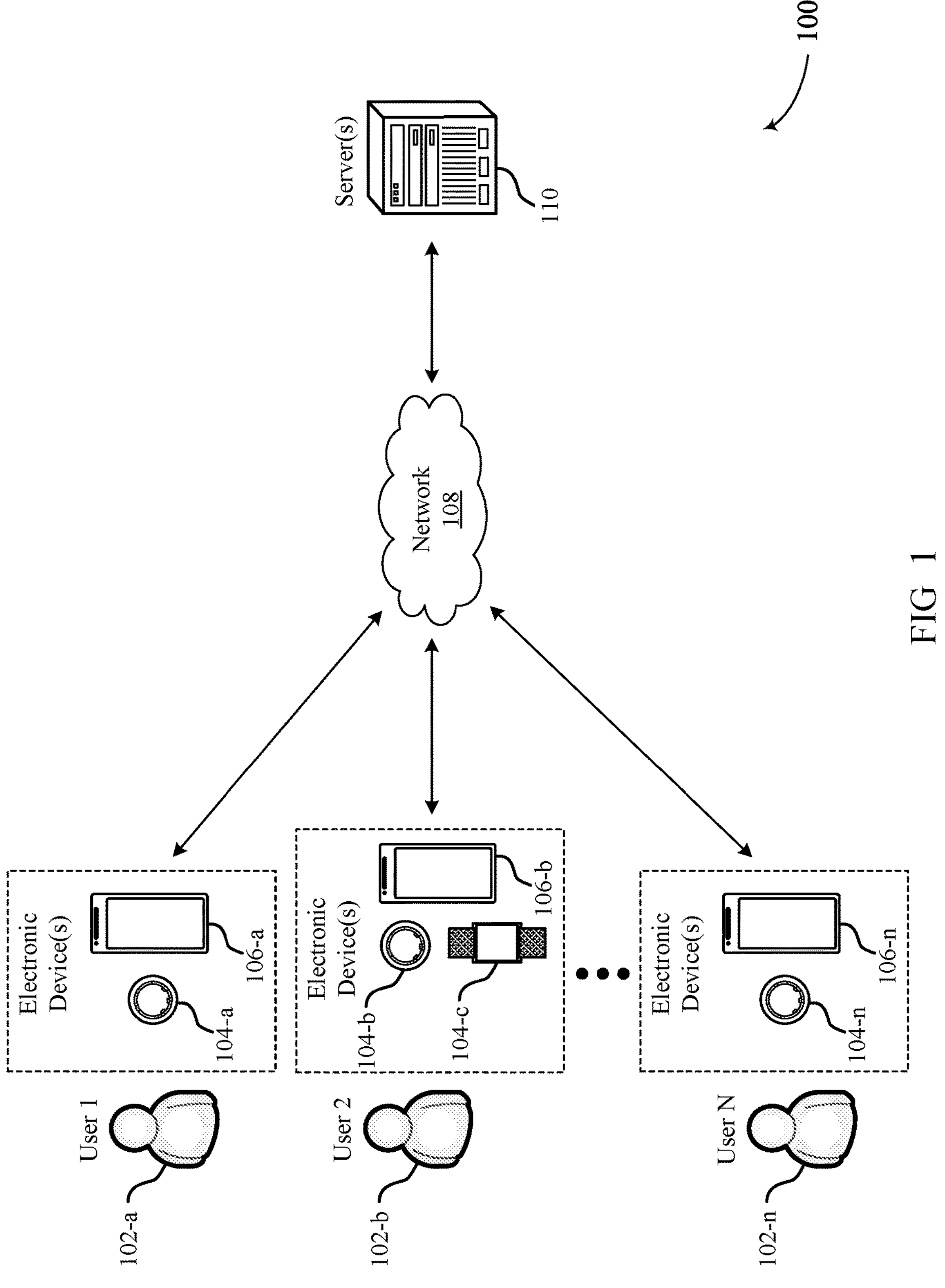
FIG. 1 illustrates an example of a system that supports techniques for measuring cumulative stress using wearable-based data in accordance with aspects of the present disclosure.

Some wearable devices may be configured to collect physiological data from users, such as temperature data, heart rate data, and the like. For example, a wearable device may collect heart rate measurements and corresponding heart rate variability (HRV) measurements from a user, where HRV is a measure of fluctuation (e.g., variability) of time intervals between adjacent heartbeats. HRV may be used to calculate various physiological parameters, such as the quality of the user's sleep. Further, there may be a correlation between a user's HRV data, and a relative level of stress or relaxation of the user.

However, while some wearable devices may utilize HRV as an input to evaluate a relative quality of a user's sleep, such wearable devices have been unable to calculate a user's stress level. In particular, HRV data may not be sufficiently accurate to calculate a stress level of the user due to motion of the user causing errors in heart rate data from insufficient skin contact between sensors of the wearable device and the tissue of the user.

Accordingly, aspects of the present disclosure are directed to systems and methods for evaluating various stress-related metrics associated with a user, including (1) acute stress, (2) cumulative stress, and (3) resilience to stress. For the purposes of the present disclosure, the term "acute stress" may refer to a "real time" indication of the user's stress while the user is awake and sedentary. Comparatively, the term "cumulative stress" may refer to a sum total stress experienced by the user over an extended period of time, such as a period of weeks or months. Lastly, the term "resilience to stress" may refer to an ability of the user to cope with and recover from stress.

As described herein, a user device, a wearable device, or both may calculate an acute stress level of the user based on comparing a user's daytime HRV to the user's baseline daytime HRV. That is, some aspects of the present disclosure focus on determining a real time indication of the user's stress. In some examples, a wearable device may determine a baseline daytime HRV value for a user by computing a weighted average of a daily median daytime HRV value over a rolling reference window. For example, the wearable device may collect daily HRV measurements over a duration, such as three weeks. The wearable device may determine a user is awake and sedentary via sensor data, and may perform the measurements accordingly to improve accuracy of the measurements.

The system may calculate an acute stress level for the user by comparing a current daytime HRV value to the user's baseline daytime HRV value. The wearable may measure the HRV periodically throughout a day to obtain the current daytime HRV value of the user. As will be described in further detail herein, the system may use a machine learning model to fill in missing or inaccurate data (e.g., use a machine learning model to fill in missing or inaccurate HRV measurements). In some cases, the system may determine a difference between the current daytime HRV value and the baseline daytime HRV value for the user, and may compare the difference to a stress threshold and a recovery threshold to determine an acute stress metric for the user. For example, if the difference between the current daytime HRV value and the baseline daytime HRV value exceeds the stress threshold, the user may be in a state of stress. In some other examples, if the difference between the current daytime HRV value and the baseline daytime HRV value is below the recovery threshold, the user may be in a state of recovery. Specifically, if a user's daytime HRV is below a stress threshold, a system may classify the time interval as being associated with stress. Conversely, if a user's daytime HRV exceeds a recovery threshold, the system may classify the time interval as being associated with recovery. In some cases, the stress threshold and the recovery threshold may be the same value. In some other cases, the stress threshold and the recovery threshold may be different, and there may be one or more corresponding states in between the stress state and the recovery state. For instance, in some cases, the stress threshold and the recovery threshold may have the same absolute value, but may have opposite signs (e.g., +, −). The user device may display the acute stress level to the user using a graphical user interface (GUI). A user may alter one or more behaviors in accordance with the acute stress level, such as to reduce stress, which may help improve their overall health based on the current mental, physical, and emotional state of the user.

Additional or alternative aspects of the present disclosure are directed to techniques for evaluating a cumulative stress level of the user over an extended period of time, such as a period of weeks or months. In some cases, a wearable device may collect baseline HRV data over a duration, and may determine separate baseline HRV values and/or ranges for the user during the day and during the night. The daytime values and/or range may be referred to as a daytime baseline HRV and the nighttime values and/or range may be referred to as a nighttime baseline HRV. The wearable device may collect HRV data from the user over multiple days and nights, using a machine learning model to fill in missing or inaccurate data. The wearable device may send the acquired HRV data to a user device.

The user device, the wearable device, or both, may compare the acquired HRV data to the applicable baseline HRV values, where HRV data collected during the day (e.g., while the user is awake) is compared to the user's daytime baseline HRV, and where HRV data collected at night (e.g., while the user is asleep) is compared to the user's nighttime baseline HRV. By comparing the daytime and nighttime HRV data to corresponding baseline HRV data, the system may calculate a stress level of the user for each day. Over time, the calculated stress levels may be compared with one another to observe long-term stress (e.g., cumulative stress) experienced by the user, which may be used to predict burn-out, identify chronic illness, etc. In some cases, a user device may display a cumulative stress level to the user (e.g., an indication of the long-term stress experienced by the user) using a GUI by comparing the stress level from the previous day to a stress level for the current day. A user may alter one or more behaviors in accordance with the cumulative stress level, such as to reduce the risk of burn-out, chronic illness, etc., which may help improve their overall health based on the current mental, physical, and emotional state of the user.

Additional or alternative aspects of the present disclosure are directed to techniques for evaluating a user's resilience to stress (e.g., how well the user copes with and/or recovers from stress). That is, a user device, a wearable device, or both, may calculate a stress resilience score for a user based on comparing a stress level, a daytime recovery, and a sleep recovery of the user for a time period spanning multiple days (e.g., a two week period). The stress resilience score may indicate how well a user is able to handle and recover from stress. For example, for each 24-hour period of a two-week time interval, the wearable device may acquire physiological data to determine an aggregate stress index for the respective day, where the aggregate stress index includes a daytime stress level for the respective day, a daytime recovery level for the respective day, and a sleep recovery level for the corresponding night.

In some cases, the system may determine a resilience score for the user by calculating a weighted sum of the aggregate stress indices for the two-week period, where the weights for the aggregate stress indices are assigned according to a recency of the data (e.g., aggregate stress indices for more recent days are weighted more heavily). The user device may provide feedback to the user in accordance with the resilience score. For example, the user device may provide the user instructions regarding how the user may improve a resilience score, or positive feedback instructing the user to maintain a current resilience score. A user may alter one or more behaviors in accordance with the instructions, which may help improve their ability to endure stress, and improve their overall health based on the current mental, physical, and emotional state of the user.

Aspects of the disclosure are initially described in the context of systems supporting physiological data collection from users via wearable devices. Additional aspects of the disclosure are described in the context of example process flows and example GUIs. Aspects of the disclosure are further illustrated by and described with reference to apparatus diagrams, system diagrams, and flowcharts that relate to techniques for measuring cumulative stress using wearable-based data.

FIG. 1 illustrates an example of a system 100 that supports techniques for measuring cumulative stress using wearable-based data in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, HRV, actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the system 200 may support calculating stress related parameters. For example, the system 200 may support calculating an acute stress level, a cumulative stress level, a stress resilience score, or any combination thereof for a user. In particular, techniques described herein support a wearable device 104, such as a wearable ring device 104 as described with reference to FIG. 1. For example, a wearable device 104 may include an inner housing 205 configured to house a sensor module that includes one or more sensors that are configured to acquire physiological data from a user 102. The one or more sensors of the wearable device 104 may obtain physiological measurements from the user (e.g., temperature sensors, additional LED-PD sensors used for measuring heart rate, oxygen saturation, one or more sensors that a device may use to detect whether a user is asleep, active, or the like).

For example, the one or more sensors of the wearable device 104 may acquire physiological data from a user throughout one or more time intervals, where the physiological data may include heart rate data, motion data, or both. In some examples, the time intervals may occur when the user is sedentary and awake. Additionally, or alternatively, the time intervals may include an awake interval during which the user is awake and an asleep interval during which the user is asleep. The user device 106 may receive the physiological data (e.g., including the physiological data measured during the one or more time intervals) from the wearable device 104.

In some cases, the one or more sensors of the wearable device 104 are configured to acquire the physiological data from the user based on arterial blood flow, body temperature, etc. In some implementations, the one or more sensors of the wearable device 104 are configured to acquire the physiological data (e.g., including PPG data) from the user based on blood flow that is diffused into the microvascular bed of skin with capillaries and arterioles. The one or more sensors of the wearable device 104 may be an example of photodetectors from the PPG system 235, temperature sensors 240, motion sensors 245, galvanic sensors, and other sensors.

While much of the present disclosure describes one or more components in the context of a wearable ring device, aspects of the present disclosure may additionally or alternatively be implemented in the context of other wearable devices. For example, in some implementations, the one or more components described herein may be implemented in the context of other wearable devices, such as bracelets, watches, necklaces, piercings, and the like. For example, the wearable device 104 may surround a finger, wrist, ankle, earlobe, or the like of a user.

For example, as noted previously herein, the wearable device 104 of the system 200 may be worn by a user to collect data from the user, including temperature data, sleep data, recovery data, activity data, heart rate data, HRV data, respiratory rate data, blood pressure data, blood glucose data, and the like. The wearable device 104 of the system 200 may collect the physiological data from the user based on temperature sensors and measurements extracted from arterial blood flow (e.g., using PPG signals). In some cases, the wearable device 104 may collect the physiological data from the user based on measurements extracted from capillary blood flow, arteriole blood flow, or both. The physiological data may be collected continuously.

In some implementations, the one or more sensors of the wearable device 104 may sample the user's temperature continuously throughout the day and night. Sampling at a sufficient rate (e.g., one sample per minute) throughout the day and/or night may provide sufficient temperature data for analysis described herein. In some implementations, the wearable device 104 may continuously acquire temperature data (e.g., at a sampling rate). In some examples, even though temperature is collected continuously, the system 200 may leverage other information about the user that it has collected or otherwise derived (sleep stage, activity levels, illness onset, stress, etc.) to select a representative temperature for a particular day that is an accurate representation of the underlying physiological phenomenon.

In some aspects, physiological data collected via the wearable devices 104 (e.g., HRV data) may be used to evaluate various stress-related metrics for the user 102, such as (1) acute stress, (2) cumulative stress, and (3) resilience to stress. As noted previously herein, for the purposes of the present disclosure, the term "acute stress" may refer to a "real time" indication of the user's stress while the user is awake and sedentary. Comparatively, the term "cumulative stress" may refer to a sum total stress experienced by the user over an extended period of time, such as a period of weeks or months. Lastly, the term "resilience to stress" may refer to an ability of the user to cope with and recover from stress.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
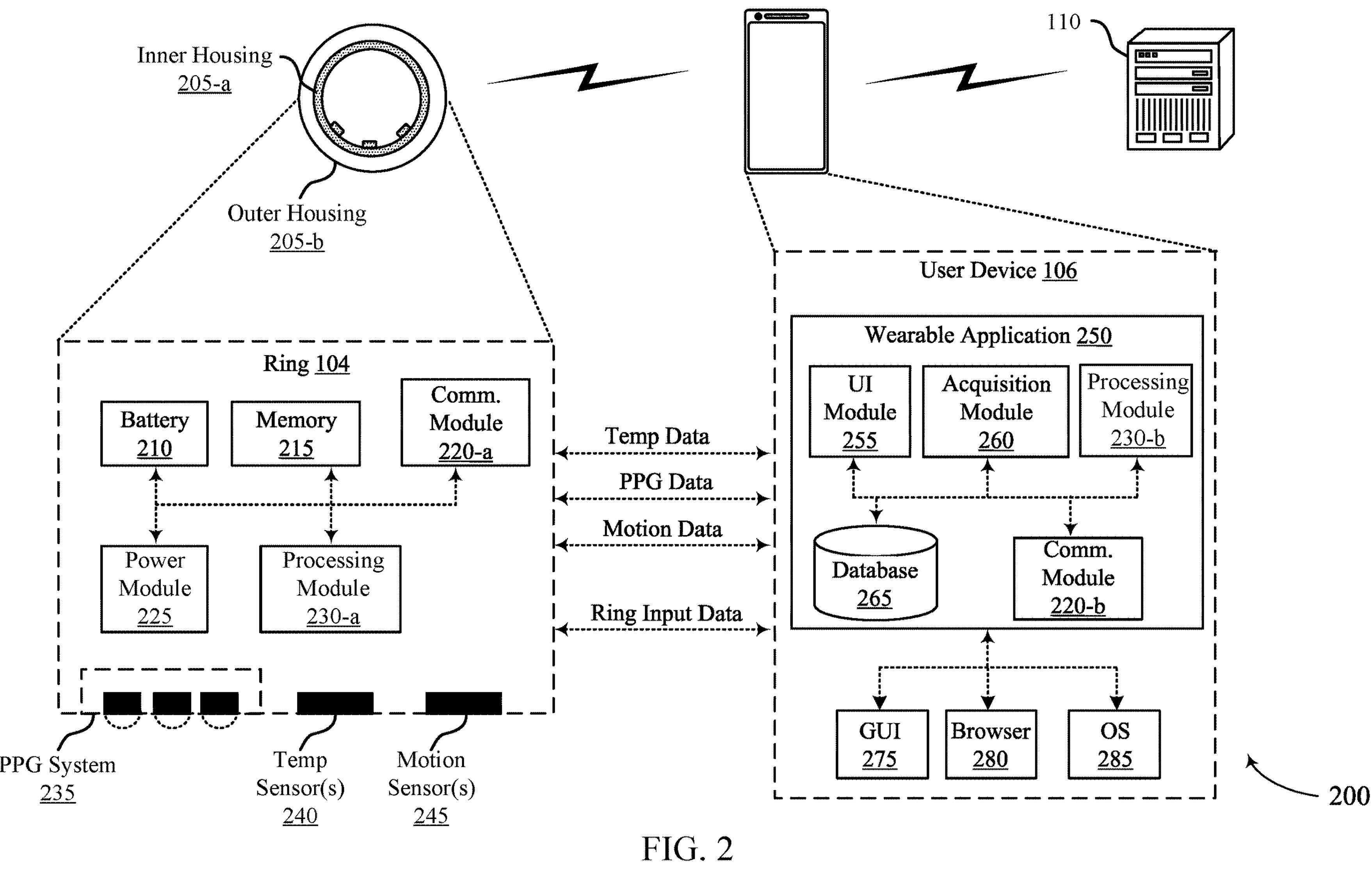
FIG. 2 illustrates an example of a system that supports techniques for measuring cumulative stress using wearable-based data in accordance with aspects of the present disclosure.

FIG. 2 illustrates an example of a system 200 that supports techniques for measuring cumulative stress using wearable-based data in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, physiological data collected via the wearable devices 104 (e.g., HRV data) of the system 200 may be used to evaluate various stress-related metrics for the user 102, such as (1) acute stress, (2) cumulative stress, and (3) resilience to stress. As noted previously herein, for the purposes of the present disclosure, the term "acute stress" may refer to a "real time" indication of the user's stress while the user is awake and sedentary. Comparatively, the term "cumulative stress" may refer to a sum total stress experienced by the user over an extended period of time, such as a period of weeks or months. Lastly, the term "resilience to stress" may refer to an ability of the user to cope with and recover from stress.

Figure 3:
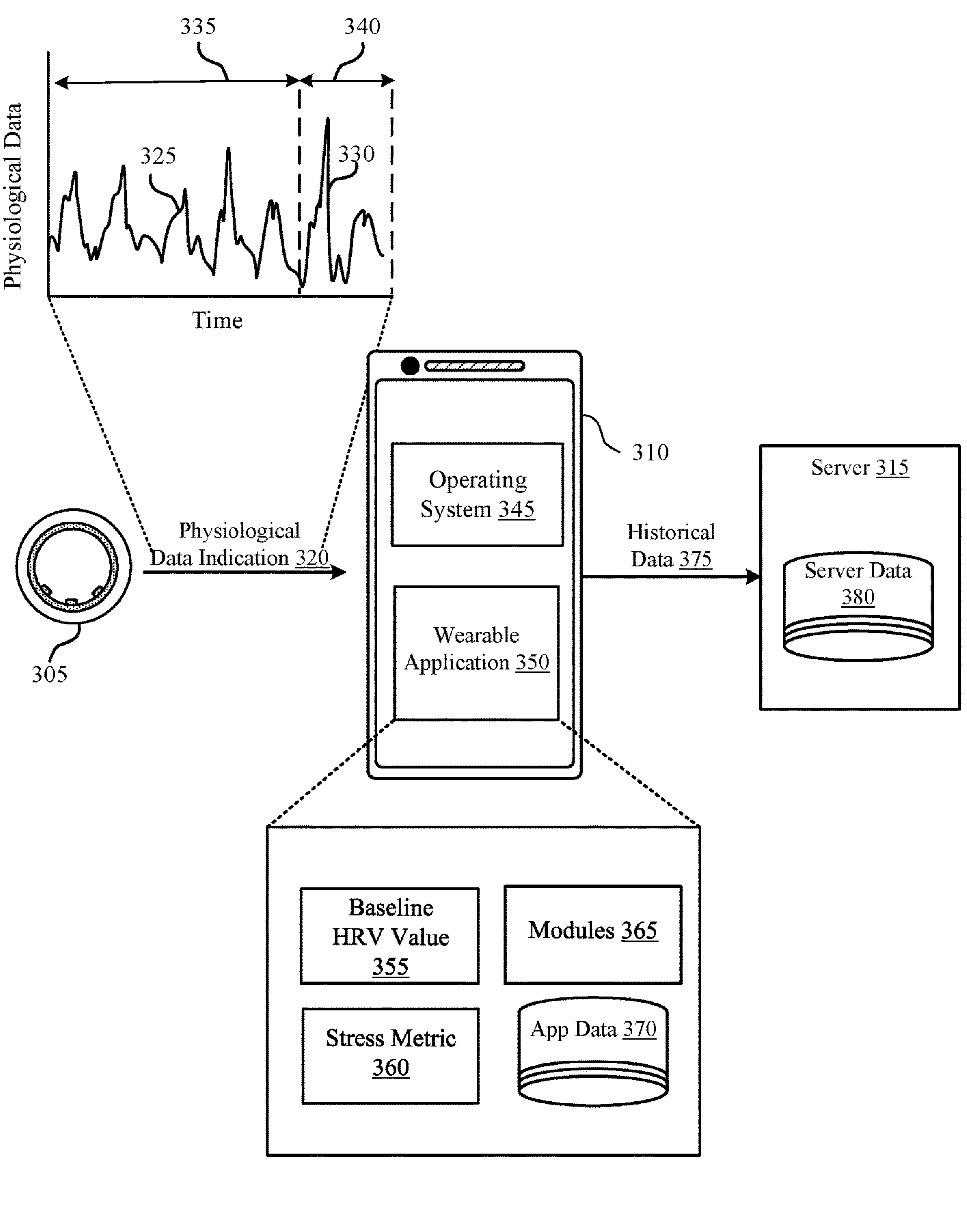
FIG. 3 shows an example of a flowchart for evaluating stress-related metrics associated with a user in accordance with aspects of the present disclosure.

FIG. 3 shows an example of a system 300 for evaluating stress-related metrics associated with a user in accordance with aspects of the present disclosure. The system 300 may implement, or be implemented by, system 100, system 200, or both. In particular, system 300 illustrates an example of a ring 305 (e.g., wearable device 104), a user device 310, and a server 315, as described with reference to FIG. 1. For example, the system 300 may be configured to evaluate various stress-related metrics associated with a user, such as acute stress, cumulative stress, and/or resilience to stress.

The ring 305 may acquire physiological data. The physiological data may include temperature data, heart rate data, respiratory rate data, HRV data, sleep data, blood oxygen data, motion data, among other forms of physiological data as described herein. The ring 305 may transmit a physiological data indication 320 to the user device 310, where the physiological data indication 320 may include the physiological data 325 and the physiological data 330. For example, the physiological data indication 320 may include HRV data for one or more time intervals. The physiological data indication 320 may include multiple transmissions of physiological data, such as a transmission for the physiological data 325 and a transmission for the physiological data 330. In some cases, multiple devices may acquire physiological data. For example, a first computing device (e.g., user device 310) and a second computing device (e.g., the ring 305) may acquire the physiological data.

For example, the ring 305 may acquire user physiological data, such as user temperature data, respiratory rate data, heart rate data, HRV data, sleep data, SpO2 data, (e.g., blood oxygen saturation), galvanic skin response, actigraphy, and/or other user physiological data. The ring 305 may acquire raw data and convert the raw data to features with daily granularity. In some implementations, different granularity input data may be used. The ring 305 may send the data to another computing device, such as a mobile device (e.g., user device 310) for further processing.

In some cases, the wearable device 305 may measure physiological data 325 (e.g., HRV data and motion data) over a reference time interval 335. The reference time interval 335 may span multiple days, multiple weeks, or any other time interval. In some cases, the physiological data 325 may be from periods when the user is sedentary and awake, which the wearable device 305, the user device 310, or both may determine from data collected at one or more sensors of the wearable device 305 (e.g., from the physiological data 325). In some other cases, the physiological data 325 may be from periods when the user is asleep.

The wearable device 305 may send the physiological data 325 to the user device 310, and the user device 310 may send the historical data 375 including the physiological data 325 to a server 315. The server 315 may store the historical data 375 as server data 380. In some cases, the wearable device 305, the user device 310, or both, may determine a baseline HRV value 355 from the physiological data 325. In some cases, the baseline HRV value 355 may be a baseline daytime HRV value if the physiological data 325 is measured when the user is sedentary and awake. In some other cases, the baseline HRV value 355 may include a first baseline HRV value of the user during periods that the user is awake and a second baseline HRV value of the user during periods that the user is asleep if the physiological data 325 is measured when the user is awake and when the user is asleep.

In some examples, the wearable device 305 may measure physiological data 330, such as for a time interval 340. The time interval 340 may occur after the time interval 335. In some cases, the time interval 340 may be relatively shorter than the time interval 335. For example, the physiological data 330 from the time interval 340 may be representative of a current physiological state of a user (e.g., measured in seconds, minutes, or hours), while the physiological data 325 from the time interval 335 may be representative of a historical physiological state of the user. In some other cases, the physiological data 330 from the time interval 340 may span multiple days and multiple nights.

In some cases, the user may be sedentary and awake throughout the time interval 340, which the wearable device 305, the user device 310, or both may determine from data collected at one or more sensors of the wearable device 305 (e.g., from the physiological data 330). In some other cases, the user may be awake during periods of the time interval 340 and asleep during other periods of the time interval 340, which the wearable device 305, the user device 310, or both, may determine from data collected at one or more sensors of the wearable device 305 (e.g., from the physiological data 330). The wearable device 305 may send the physiological data 330 to the user device 310. The user device 310 may determine one or more HRV values of the user for the time interval 340. For example, the HRV value may be a daytime HRV value if the user is sedentary and awake during the time interval 340. In some other examples, the user device 310 may determine a first set of HRV values from periods of the time interval 340 that the user is awake and a second set of HRV values from periods of the time interval 340 that the user is asleep.

In some cases, the user device 310 may access the server data 380 to obtain the baseline HRV value 355, such as the baseline daytime HRV value, the first baseline HRV value of the user during periods that the user is awake, a second baseline HRV value of the user during periods that the user is asleep, or any combination thereof. For example, the user device 310 may receive the physiological data 330 from the wearable device 305, which may trigger the user device 310 to access the baseline HRV value 355 from the physiological data 325 stored at the server 315.

In some cases, the user device 310 may compare the daytime HRV value from the physiological data 330 to the baseline daytime HRV value from the physiological data 325 to determine an acute stress level of the user. The acute stress level of the user may be representative of a relative amount of stress experienced by the user throughout the time interval 340. In other words, the acute stress level of the user may illustrate a real time or near-real-time "snapshot" of the user's stress level.

In some other cases, the user 310 may compare the first set of HRV values with the first baseline HRV value, compare the second set of HRV values with the second baseline HRV value, or both to determine a cumulative stress level of the user throughout the time interval 340. The cumulative stress level may be based on a baseline stress level, which may be calculated from the physiological data 325 over a reference time interval (e.g., the time interval 335), based on user inputs received via the user device 310, or both. The cumulative stress level may indicate a total amount of stress the user experiences throughout the time interval 340, a trend in stress level of the user throughout the time interval 340, or both.

In some other cases, the wearable device 305 may collect physiological data from a user throughout multiple time intervals, such as the time interval 335 and the time interval 340. Each time interval may span an awake interval during which the user is awake and an asleep interval during which the user is asleep, which the wearable device 305, the user device 310, or both may determine from the physiological data (e.g., heart rate data and/or motion data). The wearable device 305 may send the physiological data from the multiple time intervals to the user device 310, such as in the physiological data indication 320. The user device 310 may determine a stress index and a recovery index for each awake interval and a sleep recovery index from each asleep interval. The user device 310 may calculate a stress resilience metric of the user. For example, the user device 310 may obtain a weighted sum of the stress indices, recovery indices, and sleep recovery indices of the time intervals. The weight of each index may be correlated to a recency of each index. For example, a more recent index may have a relatively greater weight in the stress resilience metric calculation. In some cases, the stress resilience metric may indicate a relative capability of the user to cope with stress, to recover from stress, or both.

Although the system may be implemented by a ring 305 and a user device 310, any combination of computing devices described herein may implement the features attributed to the system 300. In some cases, the system 300 may smooth the data (e.g., using a 7-day smoothing window, a 90-day smoothing window, or other window). The missing values may be imputed (e.g., using the forecaster Impute method from the Python package).

The user device 310 may include the wearable application 350 and an operating system 345. The wearable application 350 may run on the operating system 345 of a user device 310 and is associated with a ring 305. The wearable application 350 may include at least modules 365 and application data 370. In some cases, the application data 370 may include historical physiological data patterns for the user and other data. The physiological data patterns may include temperature data, heart rate data, respiratory rate data, HRV data, sleep data, blood oxygen saturation data, or a combination thereof.

In some cases, the user device 310 may present a stress metric 360, a baseline HRV value 355, or both to the user via the wearable application 350. The wearable application 350 may include an application data processing module that may perform data processing. For example, the application data processing module may include modules 365 that provide functions attributed to the system 300. Example modules 365 may include a baseline HRV module, a baseline stress module, a stress metric module, and the like.

The stress metric module may calculate the stress metric 360 for the user based on the physiological data 325, the physiological data 330, or both. For example, the stress metric module may calculate an acute stress level, a cumulative stress level, a stress resilience metric, or any combination thereof. The baseline HRV module may calculate one or more baseline HRV values 355 from the physiological data (e.g., the physiological data 325). The baseline stress module may determine a baseline stress level for the user, such as from the physiological data and inputs from the user for the cumulative stress level calculation. In such cases, the system 300 may receive the physiological data indication 320 from the wearable device 305 including user physiological data and output one or more baseline HRV values 355 and a respective calculated stress metric 360 (e.g., acute stress level, cumulative stress level, stress resilience metric, or any combination thereof). The wearable application 350 may store application data 370, such as acquired physiological data.

In some cases, the user's logged symptoms (e.g., tags) in combination with the user's physiological data may characterize the baseline HRV value 355, the stress metric 360, or both. In such cases, the user's logged input may contribute to calculating the baseline HRV value 355, the stress metric 360, or both. The logged user input may be an example of an indication of a rest day, an indication of an activity target, an indication of a menstrual cycle onset day, one or more tags, or a combination thereof.

Figure 4:
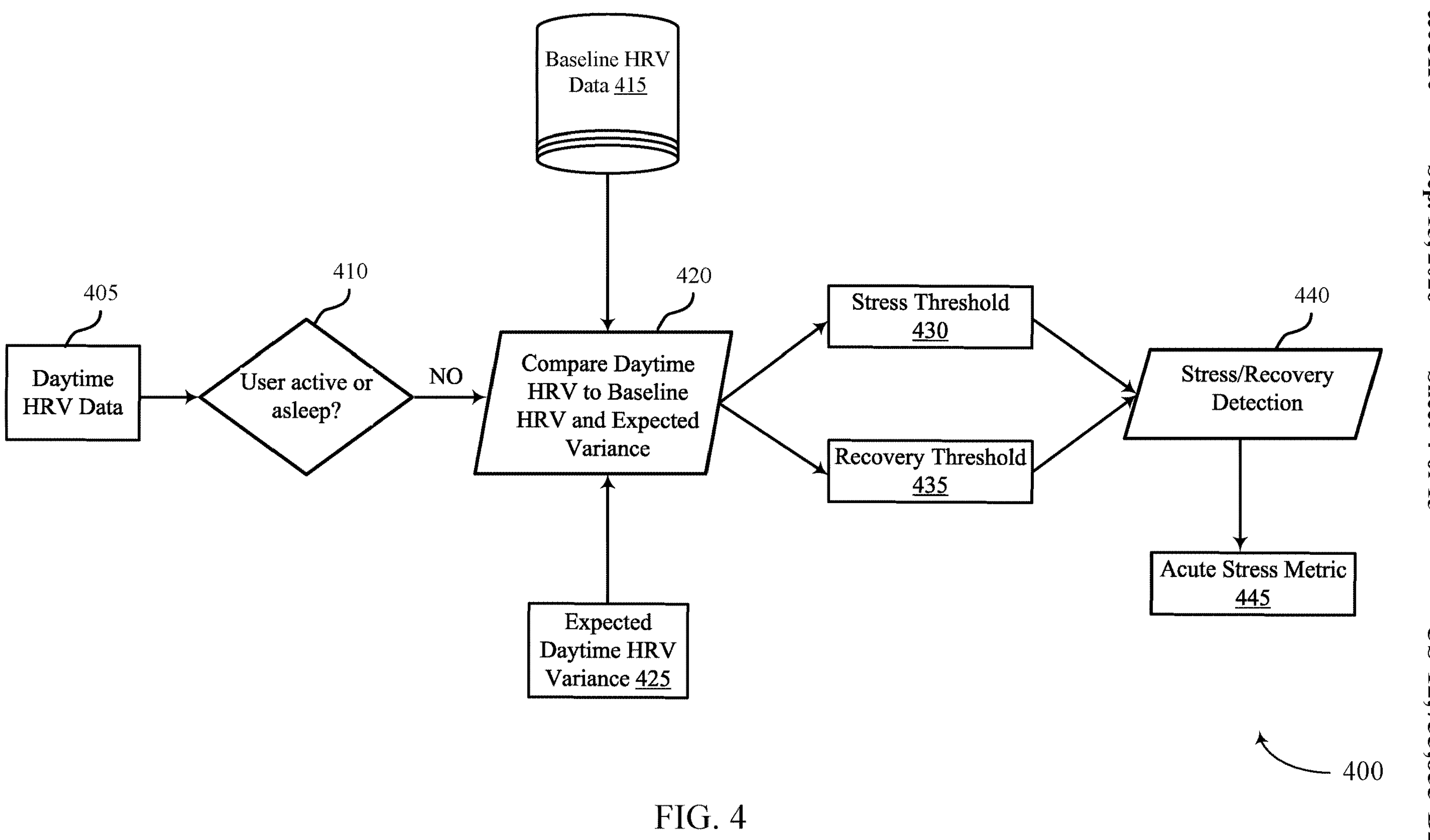
FIG. 4 shows an example of a flowchart for evaluating acute stress of a user in accordance with aspects of the present disclosure.

The system 300 may cause a GUI of the user device 310 to display the baseline HRV value 355, the stress metric 360, or both, which is described in further detail with respect to FIG. 4. The system 300 may generate a message for display on a GUI on the user device 310 that indicates the baseline HRV value 355, the stress metric 360, or both. The calculation of the baseline HRV value 355, the stress metric 360, or both may trigger a personalized message to a user highlighting the educational content associated with the baseline HRV value 355, the stress metric 360, or both. In some cases, the message may include a recommendation to rest, recommendations to improve athletic performance, a recommendation to exercise, an adjusted set of sleep targets, a quantity of calories burned, a quantity of active minutes, a quantity of steps taken by the user, a quantity of inactive minutes, a quantity of workouts to complete each week, or a combination thereof.

In some implementations, the wearable application 350 may notify the user of the baseline HRV value 355, the stress metric 360, or both and/or prompt the user to perform a variety of tasks in the activity GUI. The notifications and prompts may include text, graphics, and/or other user interface elements. The user device 310 may display notifications and prompts in a separate window on the home screen and/or overlaid onto other screens (e.g., at the top of the home screen). In some cases, the user device 310 may display the notifications and prompts on a mobile device, a user's watch device, or both.

In some implementations, the user device 310 may store historical user data 375. The historical data 375 may include historical temperature patterns of the user, historical heart rate patterns of the user, historical respiratory rate patterns of the user, historical HRV patterns of the user, historical sleep data, historical blood oxygen saturation of the user, or a combination thereof. The historical data 375 may be selected from the last few months. The historical data 375 may be used (e.g., by the user device 310 or server 315) to calculate one or more baseline HRV values 355. The historical data 375 may be used by the server 315. Using the historical data 375 may allow the user device 310 and/or server 315 to personalize the GUI by taking into consideration the user's historical data 375. In some cases, the historical data 375 may be an example of the physiological data 325.

The user device 310 may transmit historical data 375 to the server 315. In some cases, the transmitted historical data 375 may be the same historical data stored in the wearable application 350. In other examples, the historical data 375 may be different from the historical data stored in the wearable application 350. The server 315 may receive the historical data 375. The server 315 may store the historical data 375 in server data 380.

In some implementations, the user device 310 and/or server 315 may also store other data that may be an example of user information. The user information may include, but is not limited to, user age, weight, height, body mass index, and gender, and medical history of the user. In some implementations, the user information may be used as additional features for calculating the baseline HRV value 355, a baseline stress level, or both, along with the physiological data 325. The server data 380 may include the other data such as user information.

FIG. 4 shows an example of a flowchart 400 for evaluating acute stress of a user in accordance with aspects of the present disclosure. Aspects of the flowchart 400 may implement, or be implemented by, aspects of the system 100, system 200, system 300, or any combination thereof. The various steps/functions illustrated in the flowchart 400 may be implemented via a wearable device 104, a user device 106, one or more servers, or any combination thereof.

For the purposes of the present disclosure, the terms "acute stress," "acute stress metric," "acute stress level," and like terms, may refer to the strain and recovery that the user experiences while they are awake. In this regard, "acute stress" may refer to a "real time" indication of the user's stress while the user is awake and sedentary. As such, a user's "acute stress level" may include any metric or calculation that aims to capture or illustrate how the user's stress evolves throughout the day, ideally providing near real-time information about their stress levels and stress-recovery balance.

In some aspects, techniques described herein may determine an acute stress level of a user based on HRV data of the user collected via a wearable device 104. In accordance with some aspects of the present disclosure, instead of reporting HRV values as such, techniques described herein may determine an acute stress level of the user that includes a measure of how stressful the day of the member has been. In particular, movement and limitations associated with wearable devices may render some HRV calculations unreliable throughout the day. However, by combining HRV with all the other information provided by sensors and algorithms, aspects of the present disclosure may estimate how a user's activities and restorative moments have affected their acute stress level.

Reference will now be made to the flowchart 400. At 405, the system may acquire daytime HRV (DHRV) data from the user throughout the day. Direct DHRV measurements may be measured by a wearable device 104 simultaneously with daytime heart rate measurements. As such, DHRV data may be acquired at regular or irregular intervals.

At 410, the system may determine whether the user is active and/or asleep. In particular, excessive movement may cause collected physiological data (e.g., collected heart rate and/or HRV data) to be unreliable. As such, the system may determine whether the user is awake and sedentary (e.g., motion below some threshold). That is, the system may be configured to determine a user's acute stress level only at times that the user is awake and relatively stationary (e.g., heart rate below some threshold, motion below some threshold). If the user is awake and relatively stationary (e.g., step 410=NO), then the flowchart 400 may proceed to step 420.

At 420, the system may compare the user's DHRV data (e.g., HRV data collected while the user is awake and relatively sedentary) to the user's baseline HRV data 415 and/or to an expected DHRV variance 425. The baseline HRV data 415 may be specific to each respective user, and may be calculated based on physiological data previously acquired from the user (e.g., over some rolling time period, such as the previous 21 days). In such cases, the personalized baseline HRV data 415 may vary from day to day (e.g., due to the rolling reference window over which the user's baseline HRV data 415 is calculated), but may be constant for each individual day. For example, on January 22, the user's baseline HRV data 415 may be calculated by taking the median or average (or some other metric) of the user's DHRV data collected between January 1 and January 21.

For instance, for a user on a given day, the user's baseline HRV data 415 (e.g., DHRV baseline) may be computed from the directly measured DHRV values by dropping DHRV instances where hrv_accuracy is missing or hrv_accuracy=0 (e.g., only use DHRV data 405 that satisfy one or more measurement quality criteria), and dropping DHRV instances overlapping with activities or any sleep (e.g., only use DHRV data collected during periods that the user is awake and relatively stationary). In this example, the system may calculate the median DHRV of the user on each day within the baseline window (e.g., previous 21 days), and calculate the weighted average of the daily median DHRV values over the baseline window.

Additionally, the user's DHRV data 405 for a given day may be compared to an expected DHRV variance 425. The term "HRV variance," and like terms, may refer to how much the user's DHRV is expected to change or swing throughout the day. In particular, some users exhibit a relatively constant DHRV throughout the day (e.g., low expected variance), where other users may exhibit larger swings in DHRV throughout the day (e.g., high expected variance). It has been found that users with higher night-time HRV tend to have higher variation (e.g., higher expected variance) in their DHRV where users with lower nighttime HRV have lower DHRV variability (e.g., lower expected variance). This means that a DHRV deviation from the baseline (e.g., difference between DHRV data 405 and baseline HRV data 415) that indicates a strong response in a user with naturally low HRV may be insignificant in a user with naturally high HRV.

In some cases, the expected DHRV variance 425 for the user may be determined by evaluating the user's own baseline DHRV data, and/or comparing the user's physiological data to other users (e.g., comparing the user to other users within some reference group). For example, in some cases, the expected DHRV variance 425 may be calculated from a group of users within a "reference group," where users within the reference group share one or more physiological or demographic characteristics (e.g., same gender, same/similar age or activity level, etc.). In some cases, a user's average night-time HRV (e.g., nighttime HRV over the past 3 months) may be used to determine which reference group the user belongs to. After identifying the relevant reference group for the user, the system may calculate pre-defined percentile ranges (e.g., the 40th and 60th percentile, for example) DHRV for each user within the reference group, where only DHRV values with high accuracy (hrv_accuracy>80) are used. Subsequently, the system may calculate the expected DHRV variance 425 for the reference group.

Continuing with reference to the flowchart 400, the system may compare deviations between the user's DHRV data 405 and the baseline HRV data with a stress threshold 430, a recovery threshold 435, or both (e.g., ΔDHRV=current DHRV−baseline DRHV). In some cases, the stress threshold 430, recovery threshold 435, or both, may be calculated for a reference group of users based on DHRV data collected from the respective users. Subsequently, based on the comparisons, at 440 the system may perform stress/recovery detection. In other words, the system may determine whether the instant time period (e.g., current acute stress level of the user at this moment in time) may be classified as a stressful period, a recovery period, a neutral period, etc.

The ΔDHRV value of the user may be referred to as an "intensity" of the user's stress/recovery response. If ΔDHRV satisfies the stress threshold 430, the instant time period (e.g., current acute stress level) of the user may be classified as stress (e.g., stressful period). Comparatively, if ΔDHRV satisfies the recovery threshold 435, the instant time period (e.g., current acute stress level) of the user may be classified as recovery (e.g., recovery period). Otherwise, the instant time period may be classified as neutral.

Moreover, the system may compare deviations between the user's DHRV data 405 and the baseline HRV data to the user's expected DHRV variance 425 (e.g., $Var_{expected}$) to classify time periods as either a stress response (e.g., stressful period), recovery response (e.g., recovery period), and the like. For example, if $\Delta DHRV \leq -Var_{expected}$, the instant time period (e.g., current acute stress level) of the user may be classified as a stress response (e.g., stressful period). Comparatively, if $\Delta DHRV \geq Var_{expected}$, the instant time period (e.g., current acute stress level) of the user may be classified as a recovery response (e.g., recovery period). As noted previously herein, the thresholds for classifying stress and/or recovery responses may exhibit the same absolute values, but opposite signs (e.g., $\pm Var_{expected}$).

In some cases, differences between the user's DHRV data 405 and the user's baseline HRV data 415 may be scaled based on natural limits of the user's DHRV data and/or saturation points. Stated differently, in some cases, the "intensity" (ΔDHRV) between the user's DHRV data 405 and the user's baseline HRV data 415 based on saturation points for stress and recovery. Saturation points may be based on theoretical maximum and minimum DHRV values for users within some reference group, and may be used to scale a user's intensity (e.g., ΔDHRV) so that outlier DHRV values do not significantly skew the user's determined acute stress level.

Maximum and minimum DHRV values for stress and recovery can be estimated from a reference group of users, as described previously herein. In particular, saturation points for a reference group of users may be calculated as the 5th and 95th percentiles (averaged over users in each reference group) of DHRV data collected for the group of users. In practice, saturation points may be used as theoretical maximum and minimum DHRV values that cannot be exceeded, otherwise the value of the saturation point is used. In other words, if a user's DHRV data 405 exceeds the 95th percentile of DHRV data for the user, the 95th percentile of DHRV data may be used to calculate or otherwise represent the intensity (ΔDHRV) so as to not significantly skew the evaluation of the user's stress/recovery response. The stress and recovery saturation points can be summarized with respect to nighttime HRV data collected for users within a given reference group (where reference groups may be determined based on the user's average/median nighttime HRV data).

Subsequently, at 445, the system may determine an acute stress level of the user during the time interval. In particular, the system may determine the acute stress level of the user based on comparing the DHRV data 405 of the user with the baseline HRV data 415 and/or the expected DHRV variance 425. As noted previously herein, the acute stress level may be associated with a relative amount of stress experienced by the user throughout the time interval (e.g., relative amount of stress/recovery experienced by the user at this point in time).

In some implementations, the acute stress level of the user may be calculated by the wearable device 104, a user device 106, one or more servers, or any combination thereof. In some cases, the system may cause a GUI of the user device 106 to display an indication of the acute stress level, as shown and described in FIG. 5.

Figure 5:
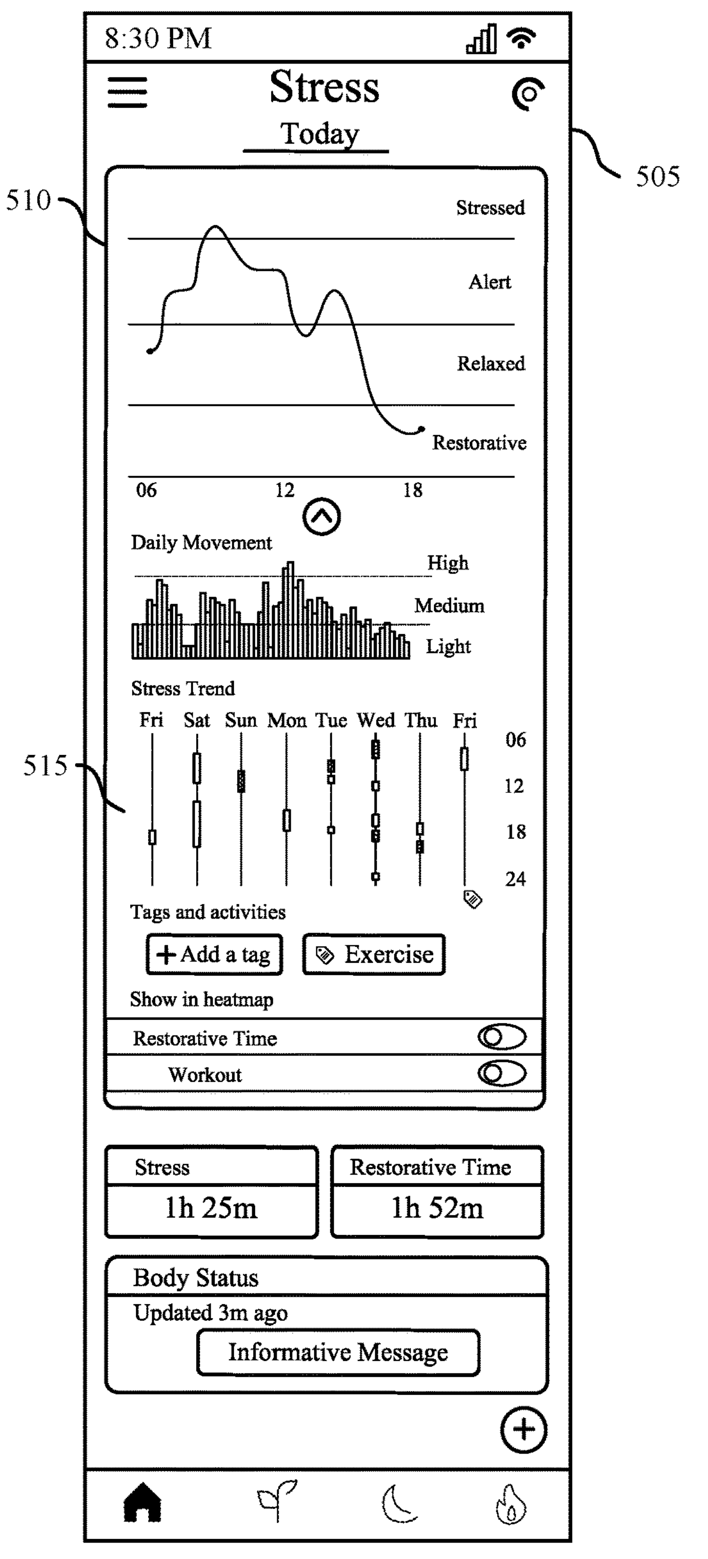
FIG. 5 shows an example of a graphical user interface (GUI) illustrating acute stress of a user in accordance with aspects of the present disclosure.

FIG. 5 shows an example of a GUI 500 in accordance with aspects of the present disclosure. Aspects of the GUI 500 may implement, or be implemented by, aspects of the system 100, system 200, system 300, flowchart 400, or any combination thereof.

In some examples, the GUI 500 illustrates an application page 505 that may be displayed to a user via the GUI 500 (e.g., GUI 275 illustrated in FIG. 2). In particular, the application page 505 illustrates information associated with an acute stress level of the user. For example, the application page 505 may include a timeline 510 that illustrates how the user's acute stress level has changed throughout the day. As noted previously herein, the system may calculate a user's acute stress level at regular or irregular intervals (e.g., every 10 minutes), and may classify each moment/time interval as representing a stressful period, a recovery period, a neutral period, or any combination thereof. For example, the timeline illustrates how the user's acute stress level has changed throughout the day between various states of stress/relaxation ranging from stressed, alert, neutral, relaxed, and restorative. Additionally, or alternatively, individual calculations/estimations of acute stress levels may be aggregated (e.g., averaged) to summarize the user's acute stress level over an interval (e.g., average acute stress level over a ten minute interval).

In some cases, the application page 505 may include a graph 515 that illustrates determined stressful periods and/or recovery periods over some time period, such as the last week. In this example, stressful periods and recovery periods may be denoted with different colors or shading within the graph 515.

In some aspects, the application page 505 may include instructions for the user to modify one or more behaviors of the user to adjust (e.g., improve) their acute stress level. In other words, the system may provide insights as to how the user can improve their acute stress level. For example, the system may suggest that the user take a nap, take a walk, or go for a bike ride to improve their acute stress level. In some cases, recommendations/insights provided by the system may be based on previous data acquired from the user. For instance, the system may recognize that the user's acute stress levels have lowered when the user went for a walk in the past, and may therefore suggest that the user go for a walk based on this previously-identified relationship. In other words, the system may determine when the user took a walk in the past based on tags inputted by the user, based on an activity logged in a third-party application, based on activity detection performed by the wearable device 104 or another component of the system. In such cases, the system may further recognize that the user's acute stress levels lowered when the user took walks in the past. By way of another example, the system may determine that the user's acute stress levels lowered when the user participated in a guided meditation within the wearable application 250 or another third-party application.

Figure 6:
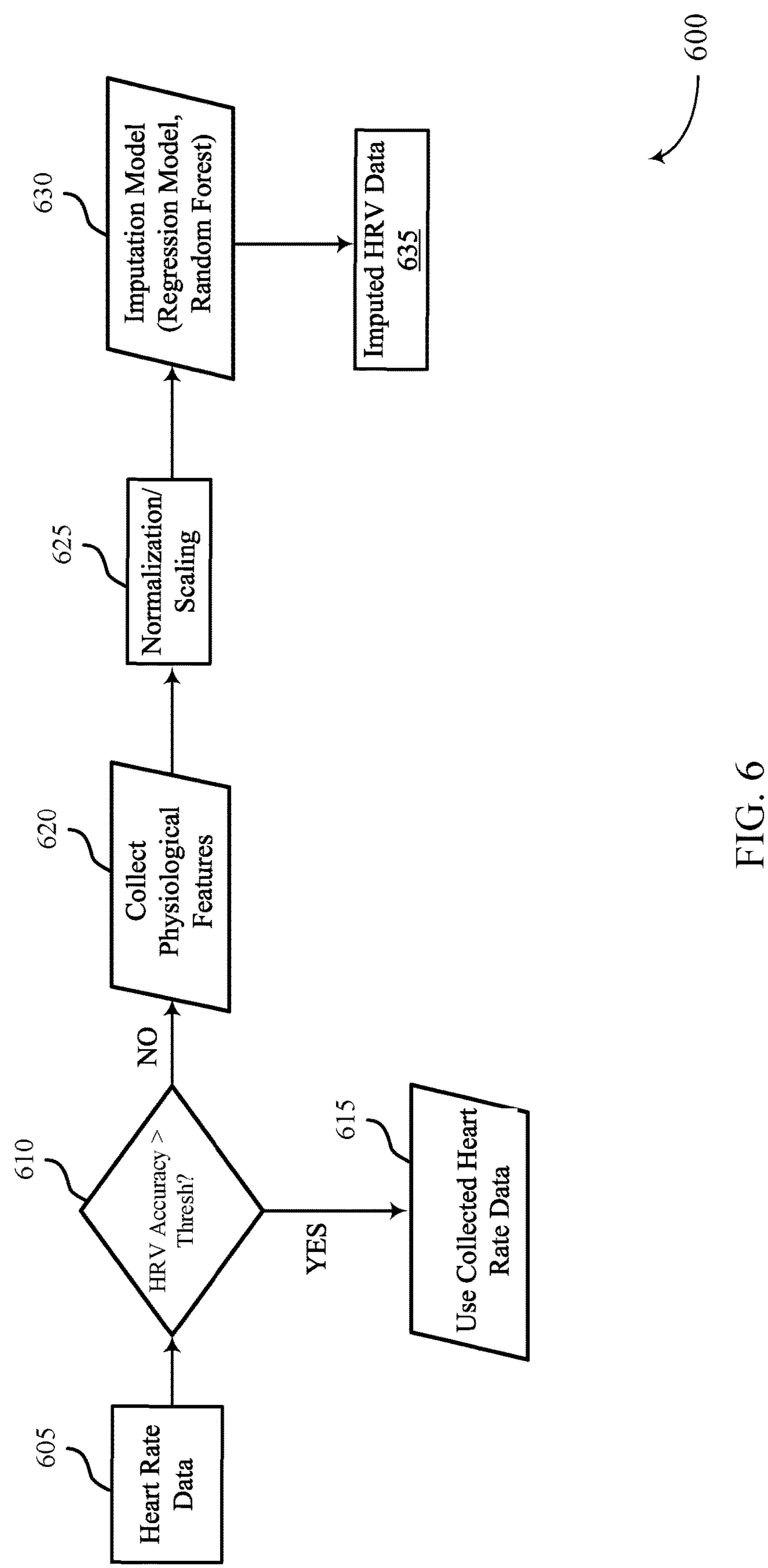
FIG. 6 shows an example of a flowchart for determining imputed heart rate variability (HRV) data in accordance with aspects of the present disclosure.

FIG. 6 shows an example of a flowchart 600 for determining imputed HRV data for a user in accordance with aspects of the present disclosure. Aspects of the flowchart 600 may implement, or be implemented by, aspects of the system 100, system 200, system 300, flowchart 400, the GUI 500, or any combination thereof. The various steps/functions illustrated in the flowchart 600 may be implemented via a wearable device 104, a user device 106, one or more servers, or any combination thereof.

As described previously herein with respect to the flowchart 400 illustrated in FIG. 4, techniques described herein may utilize DHRV data that satisfies one or more measurement quality criteria to evaluate various stress-related metrics associated with the user. In other words, the system may be configured to determine that DHRV data is of sufficient quality and/or accuracy before using the DHRV data to perform further measurements or analysis. However, movement and other conditions may result in DHRV data that does not satisfy the respective measurement quality criteria. In such cases, this low-quality DHRV data may lead to "gaps" in physiological measurements and stress-related metrics calculated for the user.

Accordingly, some aspects of the present disclosure are directed to determining "imputed" HRV values for the user in cases where acquired HRV data does not satisfy respective measurement quality criteria. HRV imputation may be carried out when a direct HRV measurement was not successful (e.g., when an HRV value is missing, or when a measurement accuracy of the HRV value is less than some threshold). In other words, HRV imputation techniques described herein may be used to estimate or predict HRV values in order to "fill in the gaps" for the user's HRV data, and may therefore be used to evaluate the user's physiological parameters when HRV cannot be calculated with sufficient quality by traditional means. In some aspects, imputed HRV values may be predicted based on other physiological parameters, such as heart rate, skin temperature, and other parameters. In this regard, HRV imputation techniques described herein may be used to calculate/predict HRV values for the user that may be used to evaluate various physiological parameters of the user even in cases where acquired HRV data is inaccurate or otherwise unreliable.

For example, the flowchart 600 illustrates a DHRV imputation model that may be used to impute/predict any missing DHRV values from other available metrics. The output is a predicted HRV value (milliseconds). In some cases, a system may implement the process/algorithm illustrated by the flowchart 600 when new daytime HR data is available for a user. However, as will be discussed in further detail herein, the process/algorithm illustrated in FIG. 6 may be interrupted if (a) a measured DHRV already exists with sufficient accuracy, or if (b) the model input features do not qualify for the prediction/imputation.

At 605, the system may acquire heart rate data from the user (e.g., using a wearable device). At 610, the system may determine HRV data associated with the user based on the acquired heart rate data, and may determine if an accuracy of the HRV data satisfies one or more thresholds. In other words, the system may determine whether or not the HRV data satisfies one or more measurement quality criteria. If the HRV data satisfies the one or more measurement quality criteria (e.g., step 610=YES), then the flowchart 600 proceeds to step 615, and the system utilizes the collected heart rate data (and corresponding HRV data) to perform physiological analysis. For instance, in cases where the HRV data satisfies the one or more measurement quality criteria (e.g., step 610=YES), then the system may utilize the HRV data as the DHRV data 405 used to evaluate an acute stress level of the user, as described with reference to FIG. 4.

Conversely, if the HRV data does not satisfy the one or more measurement quality criteria (e.g., step 610=NO), then the flowchart 600 proceeds to step 620 to perform HRV imputation. At 620, the system collects or determines other physiological features associated with the user, such as skin temperature data/features, activity data/features, respiration data/features, SpO2 data/features, MET data/features, and the like. The physiological features/data collected at 620 may be associated with information about the physiological context of the user, and may be aggregated for a particular time interval (e.g., a time interval over which HRV values fail to satisfy the measurement quality criteria), and/or aggregated over longer time periods leading to the prediction/imputation instance.

At 625, the system may normalize and/or scale the physiological data/features. For example, the system may normalize acquired heart rate data, acquired skin temperature data, or both. In some cases, the physiological data may be normalized and/or scaled based on the user's baseline physiological data, baseline physiological data associated with a group of users that share one or more common demographic characteristics with the user, or both.

At 630, the system may input the collected (and/or normalized/scaled) physiological data/features into an imputation model, which may include some machine learning model (e.g., regression model, random forest model) that is configured to output imputed HRV data 635 (e.g., predict an HRV value) based on the inputted physiological data/features. Subsequently, the imputed HRV data 635 may be used to "fill in the gaps" of the user's HRV data, and evaluate other physiological metrics associated with the user. For instance, the imputed HRV data 635 may be used as inputs to the flowchart 400 to determine an acute stress level of the user.

In some cases, the system may train the machine learning model (e.g., imputation model) to impute/predict HRV values (e.g., output imputed HRV data 635) by inputting "good" HRV data and corresponding physiological data into the model. For example, in order to train the model, the system may input baseline HRV data that satisfies the respective measurement quality criteria (e.g., "good" or "high quality" HRV data). Further, the system may input other physiological parameters of the user that were collected at the same or similar times as the baseline HRV data. In this regard, the model may "learn" that values of respective physiological parameters result in a corresponding HRV value (e.g., the model may "learn" that, when the user exhibits a skin temperature of X and a heart rate of Y, then their HRV is likely Z).

Figure 7:
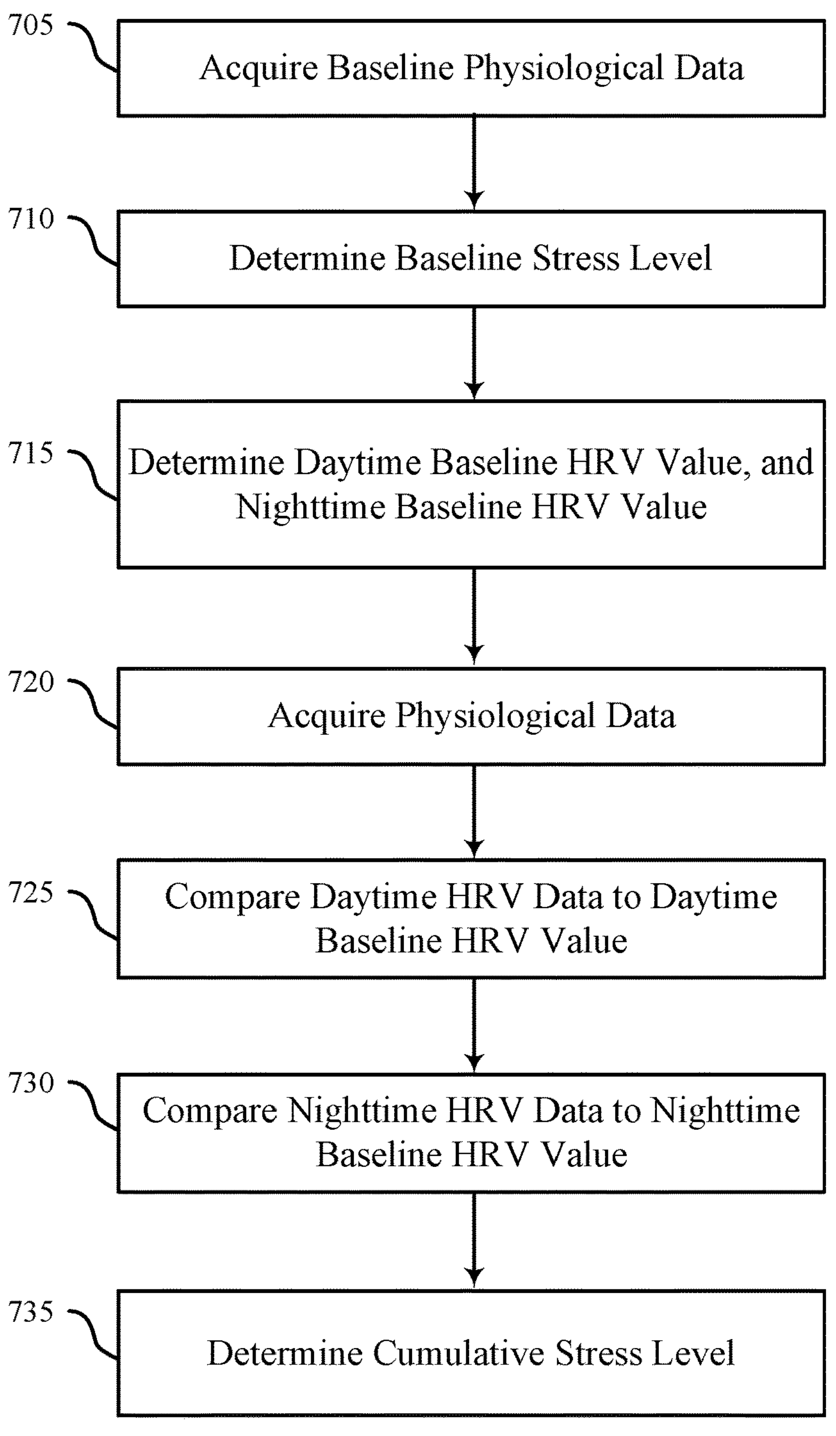
FIG. 7 shows an example of a flowchart for evaluating cumulative stress of a user in accordance with aspects of the present disclosure.

FIG. 7 shows an example of a flowchart 700 for evaluating cumulative stress of a user in accordance with aspects of the present disclosure. Aspects of the flowchart 700 may implement, or be implemented by, aspects of the system 100, system 200, system 300, flowchart 400, GUI 500, flowchart 600, or any combination thereof. The various steps/functions illustrated in the flowchart 700 may be implemented via a wearable device 104, a user device 106, one or more servers, or any combination thereof.

As compared to a user's "acute stress level," which illustrates a snapshot of the user's stress at a particular period in time while the user is awake and sedentary, cumulative stress combines daytime Stress Sensing (e.g., acute stress level) with night-time/sleep data to provide a longer-term evaluation of how much stress that the user has experienced over a period of days, weeks, or months. In some aspects, techniques for cumulative stress monitoring may be used for long-term stress monitoring, and may be used for early detection or prediction of burnout and/or chronic stress conditions.

In this regard, cumulative stress metrics described herein may be used as an "all-inclusive" stress-recovery balance indicator, which is based on (1) daytime stress (e.g., acute stress levels), (2) signs of stress in the user's sleep data, and (3) signs of recovery while the user is awake and/or asleep. In this regard, as compared to acute stress, which is based on a user's DHRV data during periods that the user is awake and sedentary, cumulative stress is based on both DHRV and nighttime HRV data for the user. That is, night-time measurements (e.g., HRV while the user is asleep) may reflect stress levels, which can be useful in determining cumulative stress.

At 705, the system may acquire baseline physiological data associated with a user (e.g., using a wearable device 104). The baseline physiological data may include baseline HRV data, baseline skin temperature data, baseline SpO2 data, baseline respiratory rate data, or any combination thereof.

At 710, the system may determine a baseline stress level for the user. In some aspects, the system may determine the baseline stress level for the user based on the baseline physiological data acquired at 710. Additionally, or alternatively, the system may determine a baseline stress level for the user based on inputs or responses received from the user. For example, the baseline stress level may be determined based on the user's answers to standardized survey questions (e.g., questionnaire), and information regarding demographic or stress-related characteristics associated with the user (e.g., previous anxiety or depression diagnosis, results of stress tests, etc.).

At 715, the system may determine a first baseline HRV value of the user during periods that the user is awake (e.g., daytime baseline HRV value), and a second baseline HRV value of the user during periods that the user is asleep (e.g., nighttime baseline HRV value). As noted previously herein, a user's HRV changes throughout the day based on the users' circadian rhythm, and is therefore different depending on whether the user is awake or asleep. As such, by determining separate baseline HRV values, techniques described herein may utilize both daytime HRV values (e.g., HRV data collected while the user is awake) and nighttime HRV values (e.g., HRV data collected while the user is asleep) to evaluate the user's cumulative stress.

As opposed to acute stress, which uses a "rolling" or "adaptive" baseline/reference window (e.g., previous 21 days) to determine the user's baseline HRV data 415, the daytime and nighttime HRV values may be determined over a longer time window (e.g., previous 4 months), and may therefore be less susceptible to change. In other words, techniques described herein used to determine a cumulative stress level of the user may use a much longer history of data in order to observe longer-term trends in the user's stress levels over a period of weeks, months, or years.

At 720, the system may acquire additional physiological data from the user (e.g., using a wearable device 104). The additional physiological data may include HRV data, skin temperature data, SpO2 data, respiratory rate data, or any combination thereof. Moreover, the additional physiological data may be collected during periods of time that the user is awake and periods of time that the user is asleep. In this regard, the additional physiological data may include daytime HRV data/values that are measured (and/or imputed) based on physical data acquired while the user is awake, and nighttime HRV data/values that are measured (and/or imputed) based on physical data acquired while the user is asleep. For example, the system may acquire additional physiological data by continually collecting data from the user using a wearable device over a period of days, weeks, or months.

At 725, the system may compare daytime HRV data acquired/imputed from the user to the daytime baseline HRV value. Similarly, at 730, the system may compare nighttime HRV data acquired/imputed from the user to the nighttime baseline HRV value.

At 730, the system may determine a cumulative stress level of the user throughout the time interval based on the comparisons of the daytime and nighttime HRV values/data performed at steps 725 and 730, respectively. For instance, the system may determine one or more stress scores associated with the user throughout periods of the time interval that the user is awake based on the first comparison of the daytime HRV data with the daytime baseline HRV value at 725. Similarly, the system may determine one or more recovery scores associated with the user throughout periods of the time interval that the user is asleep based on the second comparison of the nighttime HRV data with the nighttime baseline HRV value at 730, where the cumulative stress level is based on the one or more stress scores and the one or more recovery scores.

In some aspects, the cumulative stress level may be based on the baseline stress level associated with the user which was determined at 710. As described previously herein, the cumulative stress level may be associated with a total amount of stress the user experienced throughout the time interval, a trend in a stress level of the user throughout the time interval, or both. For example, steps 720 through 735 may be performed on a daily basis to evaluate the user's stress level compared to the user's baseline stress level, where the cumulative stress level may be associated with trends (e.g., increases or decreases) in the amount of stress that the user has experienced over time.

In this regard, comparing the cumulative stress level to the baseline stress level of the user may be used to predict a burnout condition and/or chronic stress condition of the user. In other words, because the cumulative stress level is associated with a total amount of stress that the user has experienced over a time interval, the cumulative stress level may be compared to one or more thresholds (e.g., burnout threshold, chronic stress threshold) to evaluate a user's probability of burnout, and/or a user's probability of being diagnosed with chronic stress. For the purposes of the present disclosure, the term "chronic stress" may be used to refer to a physiological condition where the user experiences relatively high levels of stress over an extended period of time, whereas the term "burnout" may refer to a physiological condition where the user's stress levels impair the ability of the user to function normally. In this regard, "burnout" may result from, or be a condition/symptom of, chronic stress.

In some aspects, information associated with the cumulative stress level of the user may be displayed via a GUI of a user device 106, as shown and described in FIG. 5. For example, the user device may display how the user's cumulative stress level has changed compared to their baseline stress level over a period of weeks, months, or years. In some aspects, the user device 106 may display instructions for the user to modify one or more behaviors of the user to adjust (e.g., improve) their cumulative stress level. In other words, the system may provide insights as to how the user can improve their cumulative stress level going forward to prevent burnout and/or chronic stress conditions.

Figure 8:
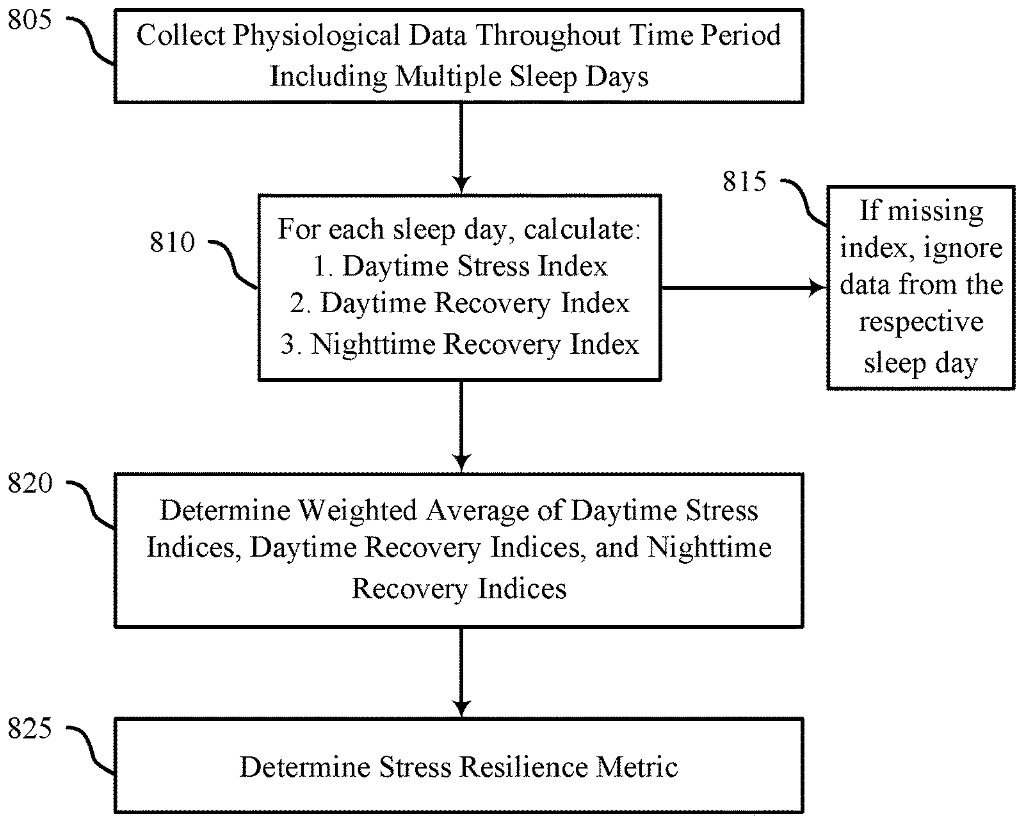
FIG. 8 shows an example of a flowchart for evaluating a user's resilience to stress in accordance with aspects of the present disclosure.

FIG. 8 shows an example of a flowchart 800 for evaluating a user's resilience to stress in accordance with aspects of the present disclosure. Aspects of the flowchart 800 may implement, or be implemented by, aspects of the system 100, system 200, system 300, flowchart 400, GUI 500, flowchart 600, flowchart 700, or any combination thereof. The various steps/functions illustrated in the flowchart 800 may be implemented via a wearable device 104, a user device 106, one or more servers, or any combination thereof.

As described previously herein, "resilience to stress" may refer to an ability of the user to cope with and recover from stress. Stress resilience acts as a defense mechanism that safeguards our ability to stay prepared. If a user exhibits robust stress resilience, the user can endure stress without it impacting the user's Readiness Score and/or other physiological characteristics. By enhancing the ability to cope with stress, a user may be able to handle higher amounts of stress and/or recover from stress more efficiently and effectively.

The concept of stress resilience is based on maintaining a balance between the amount of stress a person experiences and their ability to recover from the stress throughout the day and night. This equilibrium is crucial in ensuring that stress does not have a long-term negative impact on the person's well-being. The strength of a person's recovery is a key factor in determining their resilience to stress. A robust recovery system enables the person to quickly bounce back from stressful situations and return to a state of equilibrium.

In some aspects, resilience to stress may be based on two primary pillars: (1) how stressful is the user's daytime stress-recovery balance?, and (2) how restorative is the following sleep recovery?According to some aspects of the present disclosure, every day that a user wears a wearable device, a data point may be generated based on these two pillars in a two-dimensional coordinate plane. The x-axis may refer to the daytime stress-recovery balance (e.g., first pillar), and the y-axis may refer to the sleep recovery (second pillar). Over time, the point clouds in these two-dimensional planes may be observed to evaluate a stress resilience metric (e.g., stress resilience score, stress resilience level) for the user.

Reference will now be made to the flowchart 800 illustrated in FIG. 8. At 805, the system may collect physiological data from the user throughout a time period including multiple "sleep days," where each sleep day includes an awake interval during which the user is awake and an asleep interval during which the user is asleep. As described herein, the physiological data may be measured from the user via a wearable device 104, and may include HRV data, respiratory rate data, temperature data, activity data, SpO2 data, and the like.

At 810, the system may determine three indices for the user for each sleep day: (1) a daytime stress index, (2) a daytime recovery index, and (3) a nighttime recovery index. The first two indices (e.g., daytime stress index and daytime recovery index) relate to the first pillar for daytime stress-recovery balance, whereas the third index relates to the second pillar for sleep recovery, as described herein. In some aspects, the daily index calculation performed at 810 may be triggered each time physiological data acquired from the wearable device 104 is synced with the user device 106 (e.g., triggered each time the user opens the wearable application 250 in the morning to check their Sleep Score and Recovery Score). That is, the daily index calculation may be triggered after each sync where a long sleep has been measured (e.g., a sleep interval where the user is asleep for longer than some threshold amount of time).

In some aspects, the system may determine whether all three indices have been calculated for a respective sleep day. In other words, the system may check whether the daytime stress and recovery indices are available, as well as the nighttime recovery index for the immediately following long sleep period. Stated differently, in some implementations, the daytime stress/recovery indices for a given awake interval of a sleep day must be paired with the nighttime recovery index for the immediately following asleep interval of the sleep day. That is, the system may ensure that data collected within sleep days is not interchangeably paired up with data from different sleep days.

In some aspects the respective indices may be determined by comparing acquired physiological data to the user's own baseline physiological data, as described previously herein. For example, the daytime stress/recovery indices may be calculated based on comparing the user's DHRV data (e.g., HRV data while the user is awake) to the user's daytime baseline HRV value, and the nighttime recovery index may be calculated based on comparing the user's nighttime HRV data (e.g., HRV data while the user is asleep) to the user's nighttime baseline HRV value, as described previously herein.

Further, acute stress metrics calculated within each sleep day may be used to determine the daytime stress index and the daytime recovery index for a given sleep day. For example, the daytime stress index and the daytime recovery index (e.g., indices contributing to the first pillar for daytime stress-recovery balance) may be determined by examining the quantity of stressful periods/recovery periods during the day (as described with respect to FIG. 4), examining the intensity of stressful/recovery periods (e.g., intensity/ΔDHRV, where ΔDHRV=current DHRV−baseline DRHV), or both.

For instance, to aggregate the DHRV data of a user into the daytime stress index and the daytime recovery index, the system may analyze the user's DHRV data at multiple "stress evaluation instances" (e.g., acute stress evaluation instances) throughout a sleep day, and quantize each stress evaluation instance multiple into distinct levels of stress/recovery (e.g., high stress, moderate stress, low stress, neutral, low recovery, moderate recovery, high recovery). As described previously herein with respect to FIG. 4 describing acute stress, each instance may be classified into one of the respective levels based on how the user's DHRV data during the respective instance compares to the user's baseline DHRV data. Subsequently, having quantized the "stress evaluation instances" into the respective levels, the system may calculate a weighted sum of the "stress evaluation instances" across the respective levels. For example, high stress/recovery instances may be associated with a weight of 4, moderate stress/recovery instances may be associated with a weight of 3, low stress/recovery instances may be associated with a weight of 2, and neutral instances may be associated with a weight of 1.

Using these weights, the daytime stress index for the respective sleep day may be calculated as: Daytime Stress Index=100*(weighted sum of stress instances)/(weighted sum of stress instances+weighted sum of recovery instances+weighted sum of neutral instances). Similarly, the daytime recovery index may be calculated as: Daytime Recovery Index=100*(weighted sum of recovery instances)/(weighted sum of stress instances+weighted sum of recovery instances+weighted sum of neutral instances).

Continuing with the same example, a system may sum up how many instances, for a given sleep day, that a user exhibited varying levels of stress or recovery (e.g., how many "neutral" instances that the user was neither stressed or in recovery, how many instances where the user exhibited low recovery, how many instances where the user exhibited low stress or recovery, how many instances where the user exhibited moderate stress or recovery, how many instances that the user exhibited high stress or recovery, etc.). These observed instances may be assigned the corresponding weights and summed up, resulting in a total weighted sum of stress/recovery instances. This weighted sum of stress/recovery instances may then be used to calculate the user's daytime stress index.

Moreover, in some cases, the sleep recovery index for a given sleep day may be determined based on a weighted average of a duration of the asleep interval of the sleep day (e.g., duration of the user's longest asleep interval during a sleep day), a quality of sleep of the user during the asleep interval of the respective sleep day (e.g., Sleep Score), a resting heart rate of the user throughout the asleep interval of the respective sleep day, and an HRV variance of the HRV data collected during the asleep interval of the respective sleep day, or any combination thereof.

At 815, if the system determines that any one of the three indices are missing for a respective sleep day (e.g., due to lack of data, or due to the user not wearing the wearable device 104), the system may discard or otherwise ignore the data from that sleep day for the purposes of calculating the user's resilience to stress. For example, the user may wear a wearable ring device throughout the day (e.g., throughout an awake interval of a sleep day) so that the daytime stress index and the daytime recovery index may be calculated. However, the user may forget to charge the wearable ring device such that the wearable ring device is not able to acquire physiological data while the user sleeps that night (e.g., no data during the asleep interval of the sleep day). In this example, the system may determine that the daytime stress index and the daytime recovery index do not have a corresponding nighttime recovery index for the sleep day, and may therefore refrain from using the daytime stress/recovery indices for that sleep day when calculating the user's resilience to stress.

At 825, the system may determine weights for the respective indices calculated for the sleep days throughout a time interval. That is, for each sleep day that the system was able to calculate all three indices (e.g., daytime stress index, daytime recovery index, nighttime recovery index), the system may determine weights for the indices of a respective sleep day. In some aspects, the weights for the respective indices may be based on a recency of the respective indices. For example, daytime stress indices, daytime recovery indices, and nighttime recovery indices that were determined for a first sleep day may be weighted more heavily (e.g., have more of an impact on the user's stress resilience) as compared to the same indices calculated for a second sleep day that is further in the past. In other words, indices that are calculated more recently may be weighted more heavily when determining the user's resilience to stress.

At 825, the system may calculate a stress resilience metric (e.g., stress resilience score, stress resilience level) of the user based on the indices calculated for the respective sleep days at 810, and based on the weights determined at 820. As noted previously herein, the stress resilience metric may indicate or be associated with a relative capability of the user to cope with stress, to recover from stress, or both. In some cases, the system may only calculate the stress resilience metric for the user if there are a sufficient quantity of sleep days (e.g., 5 sleep days, 14 sleep days, etc.) for which the system has been able to calculate all three indices shown and described at 810.

In some cases, the system may classify each sleep day that was used to calculate the stress resilience metric with a stress resilience level based on comparing the stress index, the recovery index, and the sleep recovery index corresponding to the respective sleep day. In other words, as described previously herein, the system may classify each day as a stressful sleep day (e.g., stressful time interval), a recovery sleep day (e.g., recovery time interval), a neutral sleep day (e.g., neutral time interval), or any combination thereof, where an aggregation of the stress resilience levels across multiple sleep days is used to determine the stress resilience metric.

In some aspects, information associated with the stress resilience metric of the user may be displayed via a GUI of a user device 106, as will be further shown and described with reference to FIG. 9. For example, the user device 106 may display how the user's stress resilience metric has changed over time. For instance, the user device 106 may display a stress resilience metric for each sleep day (e.g., seven different stress resilience metrics across seven different sleep days). In some aspects, the user device 106 may display instructions for the user to modify one or more behaviors of the user to adjust (e.g., improve) their stress resilience metric. In other words, the system may provide insights as to how the user can improve their stress resilience metric going forward to better cope with and/or recover from stress.

Figure 9:
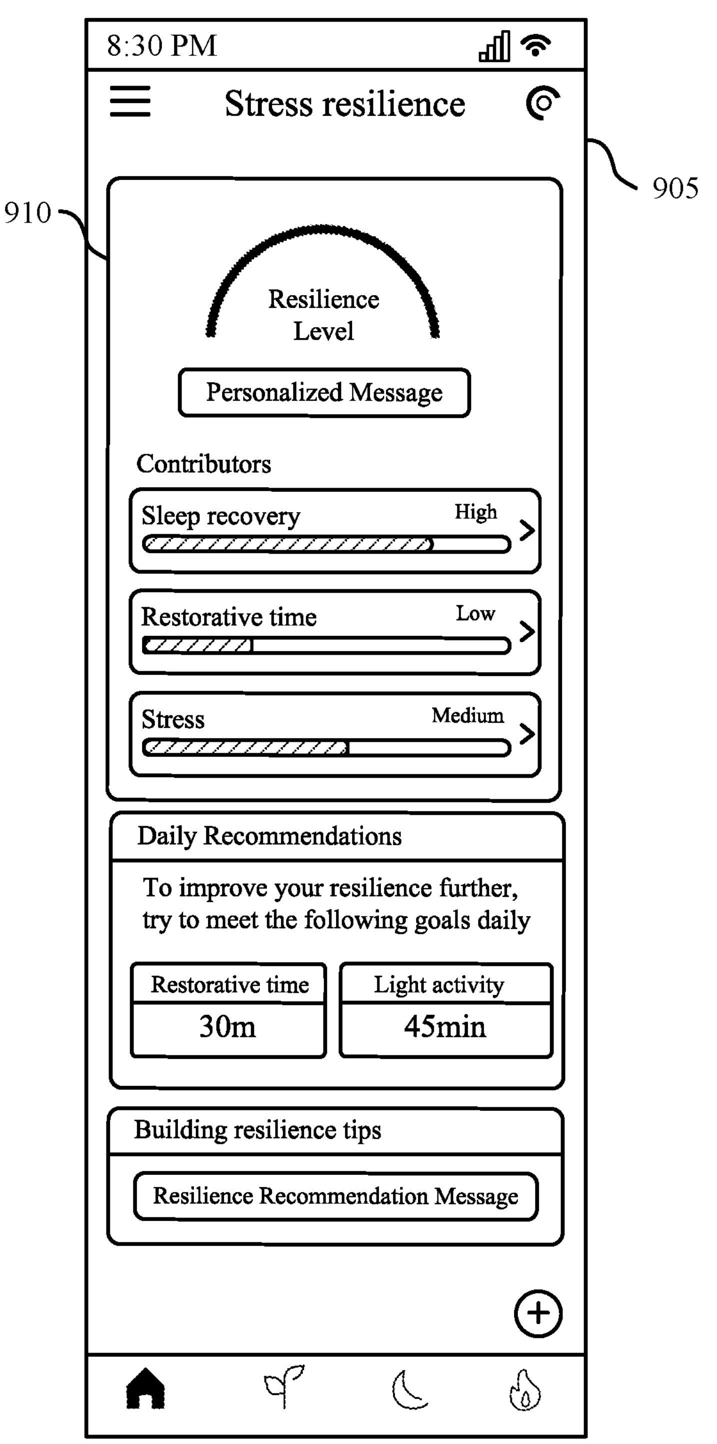
FIG. 9 shows an example of a GUI illustrating a user's resilience to stress in accordance with aspects of the present disclosure.

FIG. 9 shows an example of a GUI 900 in accordance with aspects of the present disclosure. Aspects of the GUI 900 may implement, or be implemented by, aspects of the system 100, system 200, system 300, flowchart 400, GUI 500, flowchart 600, flowchart 700, flowchart 800, or any combination thereof.

In some examples, the GUI 900 illustrates an application page 905 that may be displayed to a user via the GUI 900 (e.g., GUI 275 illustrated in FIG. 2). In particular, the application page 905 illustrates information associated with a stress resilience metric of the user. For example, the application page 905 may include a dashboard 910 that illustrates the user's stress resilience metric/score (e.g., an indication as to how well the user is able to cope with and/or recover from stress). In some cases, the dashboard 910 may illustrate the most recent stress resilience metric calculated for the user (e.g., the calculated stress resilience metric calculated from the previous sleep day). In some cases, as shown in FIG. 9, the dashboard 910 may indicate values of the three respective indices (e.g., daytime stress index, daytime recovery index, sleep recovery index) that were used to calculate the stress resilience metric.

In some aspects, the system may be configured to account for external conditions or factors (and/or the user's mental/emotional states) when evaluating the user's acute stress, cumulative stress, and/or resilience to stress. Such external conditions or factors related to the user's mental/emotional state may be determined based on tags inputted from the user, from information received from other devices or third-party applications, or any combination thereof. For example, in some cases, the system may determine that the user is dealing with anxiety, that they are on medications, that they have experienced a traumatic event, that they have experienced a loss of a family member or friend, etc. Such conditions or factors related to the user's mental/emotional states may enable the system to have a more complete view of the user's mental/emotional state, and may thereby be used to more efficiently determine the user's acute/cumulative stress levels, and/or determine how well the user is able to endure stress.

Figure 10:
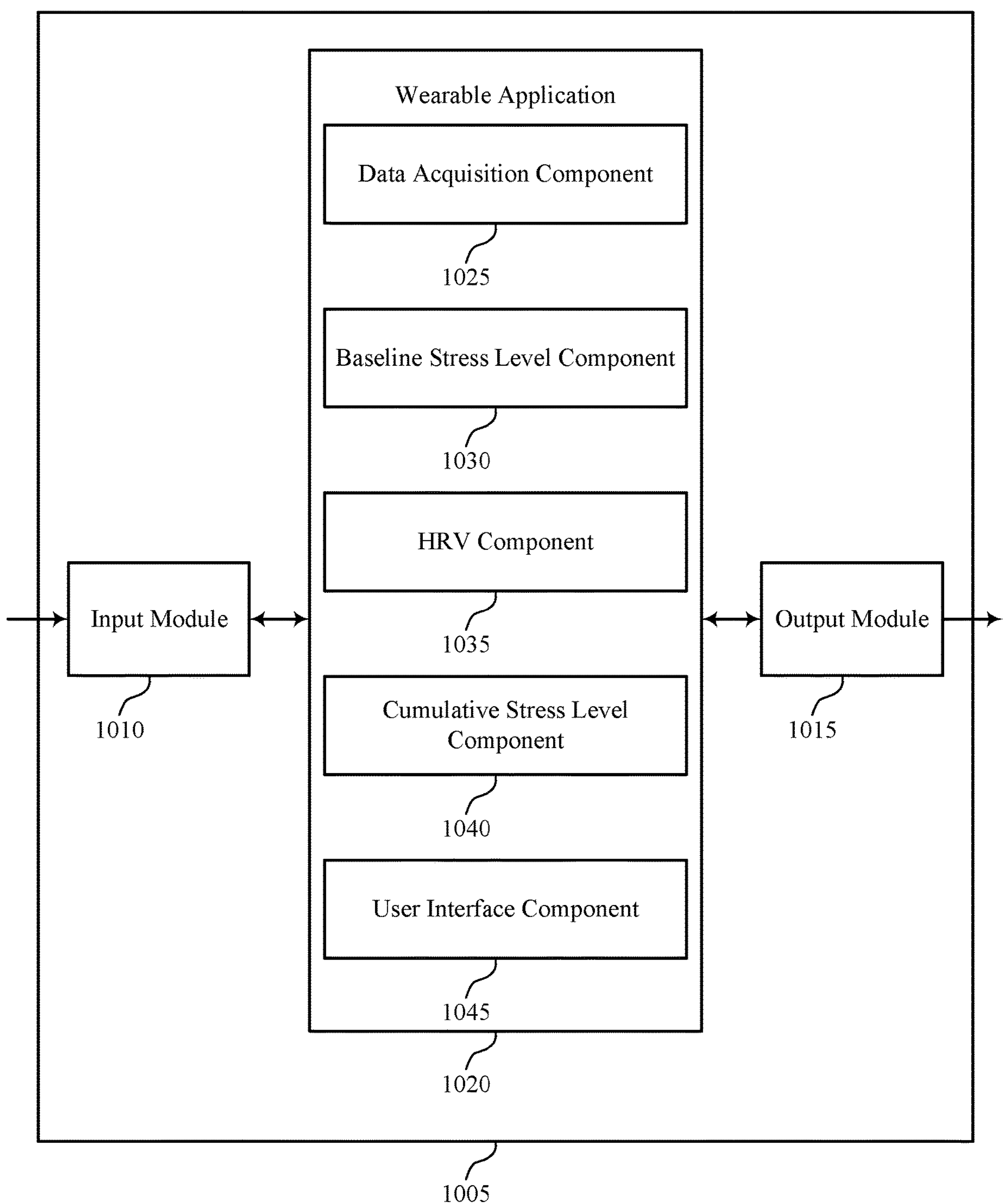
FIG. 10 shows a block diagram of an apparatus that supports techniques for measuring cumulative stress using wearable-based data in accordance with aspects of the present disclosure.

FIG. 10 shows a block diagram 1000 of a device 1005 that supports techniques for measuring cumulative stress using wearable-based data in accordance with aspects of the present disclosure. The device 1005 may include an input module 1010, an output module 1015, and a wearable application 1020. The device 1005, or one of more components of the device 1005 (e.g., the input module 1010, the output module 1015, and the wearable application 1020), may include at least one processor, which may be coupled with at least one memory, to support the described techniques. Each of these components may be in communication with one another (e.g., via one or more buses).

The input module 1010 may provide a means for receiving information such as packets, user data, control information, or any combination thereof associated with various information channels (e.g., control channels, data channels, information channels related to illness detection techniques). Information may be passed on to other components of the device 1005. The input module 1010 may utilize a single antenna or a set of multiple antennas.

The output module 1015 may provide a means for transmitting signals generated by other components of the device 1005. For example, the output module 1015 may transmit information such as packets, user data, control information, or any combination thereof associated with various information channels (e.g., control channels, data channels, information channels related to illness detection techniques). In some examples, the output module 1015 may be co-located with the input module 1010 in a transceiver module. The output module 1015 may utilize a single antenna or a set of multiple antennas.

For example, the wearable application 1020 may include a data acquisition component 1025, a baseline stress level component 1030, an HRV component 1035, a cumulative stress level component 1040, a user interface component 1045, or any combination thereof. In some examples, the wearable application 1020, or various components thereof, may be configured to perform various operations (e.g., receiving, monitoring, transmitting) using or otherwise in cooperation with the input module 1010, the output module 1015, or both. For example, the wearable application 1020 may receive information from the input module 1010, send information to the output module 1015, or be integrated in combination with the input module 1010, the output module 1015, or both to receive information, transmit information, or perform various other operations as described herein.

The data acquisition component 1025 may be configured as or otherwise support a means for acquiring baseline physiological data from the user via a wearable device. The baseline stress level component 1030 may be configured as or otherwise support a means for determining a baseline stress level associated with the user based at least in part on the baseline physiological data, one or more user inputs received via a user device, or both. The HRV component 1035 may be configured as or otherwise support a means for determining, based at least in part on the baseline physiological data, a first baseline HRV value of the user during periods that the user is awake, and a second baseline HRV value of the user during periods that the user is asleep. The data acquisition component 1025 may be configured as or otherwise support a means for acquiring additional physiological data from the user via the wearable device throughout a time interval that spans a plurality of days and a plurality of nights. The HRV component 1035 may be configured as or otherwise support a means for determining, based at least in part on the additional physiological data, a first set of HRV values of the user during periods of the time interval that the user is awake, and a second set of HRV values of the user during periods of the time interval that the user is asleep. The cumulative stress level component 1040 may be configured as or otherwise support a means for determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both. The user interface component 1045 may be configured as or otherwise support a means for displaying, to the user via a GUI of the user device, a visual representation of the cumulative stress level.

Figure 11:
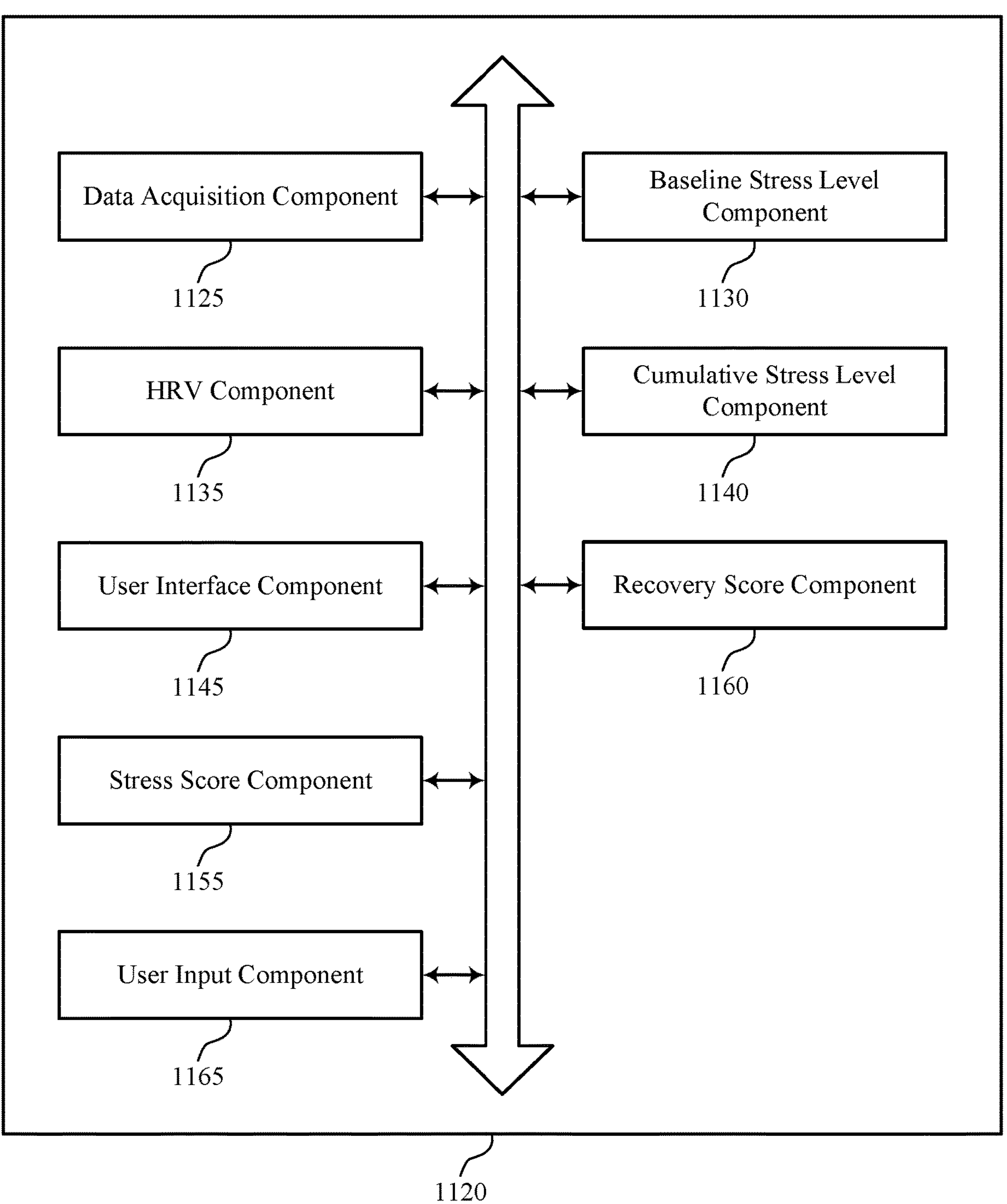
FIG. 11 shows a block diagram of a wearable application that supports techniques for measuring cumulative stress using wearable-based data in accordance with aspects of the present disclosure.

FIG. 11 shows a block diagram 1100 of a wearable application 1120 that supports techniques for measuring cumulative stress using wearable-based data in accordance with aspects of the present disclosure. The wearable application 1120 may be an example of aspects of a wearable application or a wearable application 1020, or both, as described herein. The wearable application 1120, or various components thereof, may be an example of means for performing various aspects of techniques for measuring cumulative stress using wearable-based data as described herein. For example, the wearable application 1120 may include a data acquisition component 1125, a baseline stress level component 1130, an HRV component 1135, a cumulative stress level component 1140, a user interface component 1145, a stress score component 1155, a recovery score component 1160, a user input component 1165, or any combination thereof. Each of these components, or components of subcomponents thereof (e.g., one or more processors, one or more memories), may communicate, directly or indirectly, with one another (e.g., via one or more buses).

The data acquisition component 1125 may be configured as or otherwise support a means for acquiring baseline physiological data from the user via a wearable device. The baseline stress level component 1130 may be configured as or otherwise support a means for determining a baseline stress level associated with the user based at least in part on the baseline physiological data, one or more user inputs received via a user device, or both. The HRV component 1135 may be configured as or otherwise support a means for determining, based at least in part on the baseline physiological data, a first baseline HRV value of the user during periods that the user is awake, and a second baseline HRV value of the user during periods that the user is asleep. In some examples, the data acquisition component 1125 may be configured as or otherwise support a means for acquiring additional physiological data from the user via the wearable device throughout a time interval that spans a plurality of days and a plurality of nights. In some examples, the HRV component 1135 may be configured as or otherwise support a means for determining, based at least in part on the additional physiological data, a first set of HRV values of the user during periods of the time interval that the user is awake, and a second set of HRV values of the user during periods of the time interval that the user is asleep. The cumulative stress level component 1140 may be configured as or otherwise support a means for determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both. The user interface component 1145 may be configured as or otherwise support a means for displaying, to the user via a GUI of the user device, a visual representation of the cumulative stress level.

In some examples, the stress score component 1155 may be configured as or otherwise support a means for determining one or more stress scores associated with the user throughout periods of the time interval that the user is awake based at least in part on the first comparison of the first set of HRV values with the first baseline HRV value. In some examples, the recovery score component 1160 may be configured as or otherwise support a means for determining one or more recovery scores associated with the user throughout periods of the time interval that the user is asleep based at least in part on the second comparison of the second set of HRV values with the second baseline HRV value, wherein the cumulative stress level is based at least in part on the one or more stress scores and the one or more recovery scores.

In some examples, the baseline stress level component 1130 may be configured as or otherwise support a means for determining the baseline stress level associated with the user based at least in part on the baseline physiological data, wherein the baseline physiological data comprises heart rate data, respiratory rate data, skin temperature data, or any combination thereof, and wherein determining the cumulative stress level is based at least in part on the baseline stress level.

In some examples, the cumulative stress level component 1140 may be configured as or otherwise support a means for predicting a burnout condition of the user, a chronic stress condition of the user, or both, based at least in part on a comparison between the cumulative stress level and the baseline stress level associated with the user. In some examples, the user interface component 1145 may be configured as or otherwise support a means for causing the GUI of the user device to display an alert associated with the burnout condition, the chronic stress condition, or both.

In some examples, the user input component 1165 may be configured as or otherwise support a means for receiving, from the user device, the one or more user inputs comprising one or more characteristics associated with the user, wherein determining the baseline stress level is based at least in part on the user input.

In some examples, the data acquisition component 1125 may be configured as or otherwise support a means for acquiring additional baseline physiological data associated with a plurality of users associated with a set of characteristics that are common between the plurality of users and the user. In some examples, the baseline stress level component 1130 may be configured as or otherwise support a means for determining a plurality of baseline stress levels associated with the plurality of users, wherein determining the baseline stress level associated with the user is based at least in part on determining the plurality of baseline stress levels and a comparison between the baseline physiological data associated with the user and the additional baseline physiological data associated with the plurality of users.

In some examples, to support acquiring the baseline physiological data, the user interface component 1145 may be configured as or otherwise support a means for providing, to the user via the GUI of the user device, instructions for the user to modify one or more behaviors associated with a target stress level of the user. In some examples, to support acquiring the baseline physiological data, the data acquisition component 1125 may be configured as or otherwise support a means for receiving, from the wearable device and based at least in part on providing the instructions to the user, a plurality of physiological measurements associated with the one or more behaviors. In some examples, to support acquiring the baseline physiological data, the baseline stress level component 1130 may be configured as or otherwise support a means for determining the baseline stress level associated with the user based at least in part on comparing the plurality of physiological measurements with the baseline physiological data, wherein determining the cumulative stress level is based at least in part on determining the baseline stress level.

In some examples, the visual representation indicates a relative change between a baseline stress level associated with the user and the cumulative stress level.

In some examples, the data acquisition component 1125 may be configured as or otherwise support a means for classifying a plurality of periods within time interval that the user is either awake or asleep as one of a stressful period, a recovery period, or a neutral period based at least in part on the comparison of the first set of HRV values with the first baseline HRV value and the comparison of the second set of HRV values with the second baseline HRV value, wherein determining the cumulative stress level is based at least in part on the classifying.

In some examples, the user interface component 1145 may be configured as or otherwise support a means for providing, via the GUI of the user device, feedback to the user comprising instructions for modifying one or more behaviors of the user, the one or more behaviors configured to modify the cumulative stress level of the user.

In some examples, the baseline physiological data is acquired throughout a second time interval prior to the time interval, the second time interval comprising a second plurality of days and a second plurality of nights.

In some examples, the wearable device comprises a wearable ring device.

Additionally, or alternatively, the wearable application 1120 may support measuring cumulative stress of a user over time in accordance with examples as disclosed herein. The 1150 may be configured as or otherwise support a means for acquiring baseline physiological data from the user via a wearable device. In some examples, the 1150 may be configured as or otherwise support a means for determining a baseline stress level associated with the user based at least in part on the baseline physiological data, one or more user inputs received via a user device, or both. In some examples, the 1150 may be configured as or otherwise support a means for determining, based at least in part on the baseline physiological data, a first baseline HRV value of the user during periods that the user is awake, and a second baseline HRV value of the user during periods that the user is asleep. In some examples, the 1150 may be configured as or otherwise support a means for acquiring additional physiological data from the user via the wearable device throughout a time interval that spans a plurality of days and a plurality of nights. In some examples, the 1150 may be configured as or otherwise support a means for determining, based at least in part on the additional physiological data, a first set of HRV values of the user during periods of the time interval that the user is awake, and a second set of HRV values of the user during periods of the time interval that the user is asleep. In some examples, the 1150 may be configured as or otherwise support a means for determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both. In some examples, the 1150 may be configured as or otherwise support a means for display, to the user via a GUI of the user device, a visual representation of the cumulative stress level.

Figure 12:
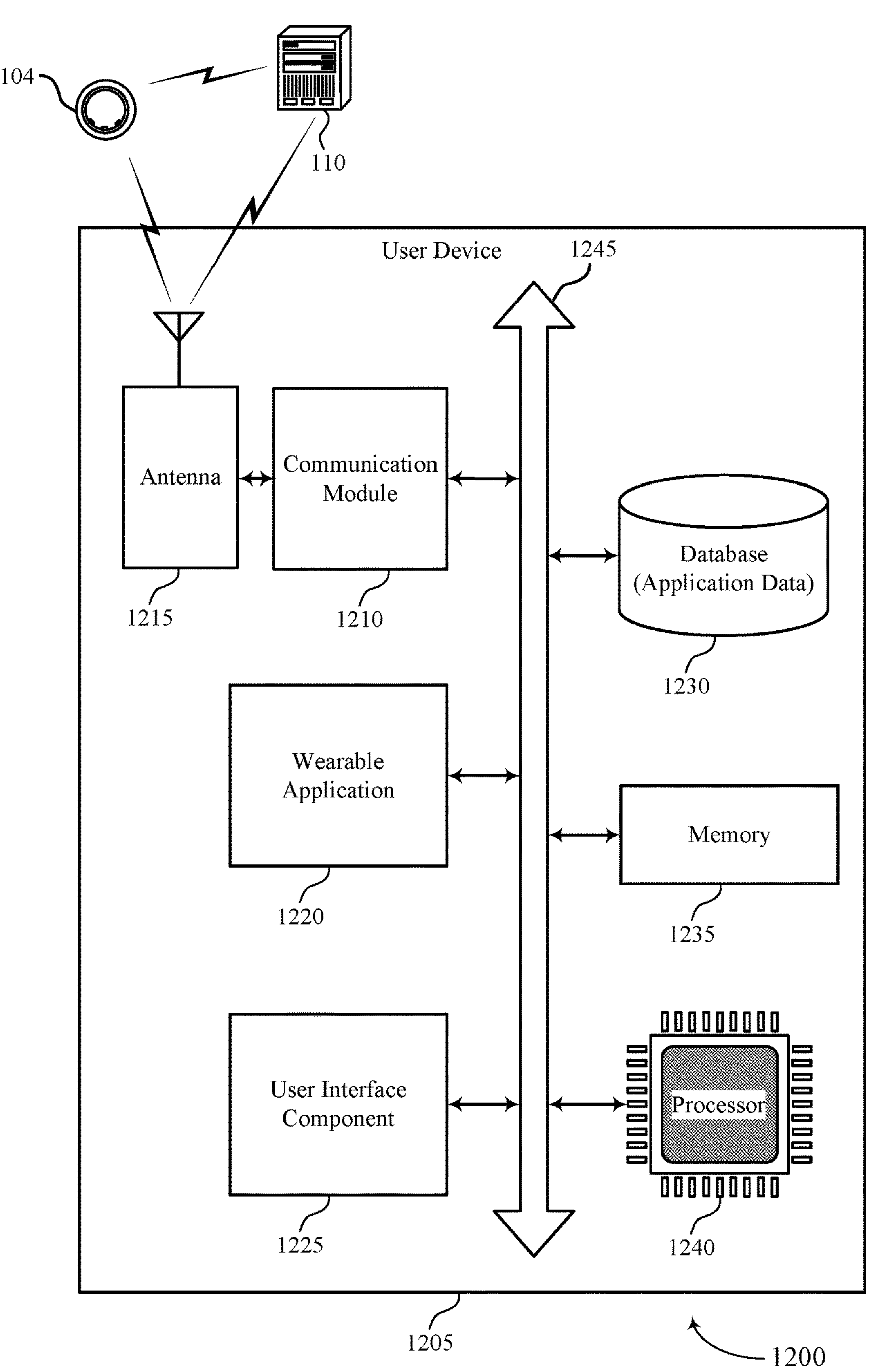
FIG. 12 shows a diagram of a system including a device that supports techniques for measuring cumulative stress using wearable-based data in accordance with aspects of the present disclosure.

FIG. 12 shows a diagram of a system 1200 including a device 1205 that supports techniques for measuring cumulative stress using wearable-based data in accordance with aspects of the present disclosure. The device 1205 may be an example of or include the components of a device 1005 as described herein. The device 1205 may include an example of a user device 106, as described previously herein. The device 1205 may include components for bi-directional communications including components for transmitting and receiving communications with a wearable device 104 and a server 110, such as a wearable application 1220, a communication module 1210, an antenna 1215, a user interface component 1225, a database (application data) 1230, at least one memory 1235, and at least one processor 1240. These components may be in electronic communication or otherwise coupled (e.g., operatively, communicatively, functionally, electronically, electrically) via one or more buses (e.g., a bus 1245).

The communication module 1210 may manage input and output signals for the device 1205 via the antenna 1215. The communication module 1210 may include an example of the communication module 220-*b* of the user device 106 shown and described in FIG. 2. In this regard, the communication module 1210 may manage communications with the ring 104 and the server 110, as illustrated in FIG. 2. The communication module 1210 may also manage peripherals not integrated into the device 1205. In some cases, the communication module 1210 may represent a physical connection or port to an external peripheral. In some cases, the communication module 1210 may utilize an operating system such as iOS®, ANDROID®, MS-DOS®, MS-WINDOWS®, OS/2®, UNIX®, LINUX®, or another known operating system. In other cases, the communication module 1210 may represent or interact with a wearable device (e.g., ring 104), modem, a keyboard, a mouse, a touchscreen, or a similar device. In some cases, the communication module 1210 may be implemented as part of the processor 1240. In some examples, a user may interact with the device 1205 via the communication module 1210, user interface component 1225, or via hardware components controlled by the communication module 1210.

In some cases, the device 1205 may include a single antenna 1215. However, in some other cases, the device 1205 may have more than one antenna 1215, which may be capable of concurrently transmitting or receiving multiple wireless transmissions. The communication module 1210 may communicate bi-directionally, via the one or more antennas 1215, wired, or wireless links as described herein. For example, the communication module 1210 may represent a wireless transceiver and may communicate bi-directionally with another wireless transceiver. The communication module 1210 may also include a modem to modulate the packets, to provide the modulated packets to one or more antennas 1215 for transmission, and to demodulate packets received from the one or more antennas 1215.

The user interface component 1225 may manage data storage and processing in a database 1230. In some cases, a user may interact with the user interface component 1225. In other cases, the user interface component 1225 may operate automatically without user interaction. The database 1230 may be an example of a single database, a distributed database, multiple distributed databases, a data store, a data lake, or an emergency backup database.

The memory 1235 may include RAM and ROM. The memory 1235 may store computer-readable, computer-executable software including instructions that, when executed, cause the processor 1240 to perform various functions described herein. In some cases, the memory 1235 may contain, among other things, a BIOS which may control basic hardware or software operation such as the interaction with peripheral components or devices.

The processor 1240 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1240 may be configured to operate a memory array using a memory controller. In other cases, a memory controller may be integrated into the processor 1240. The processor 1240 may be configured to execute computer-readable instructions stored in a memory 1235 to perform various functions (e.g., functions or tasks supporting a method and system for sleep staging algorithms).

For example, the wearable application 1220 may be configured as or otherwise support a means for acquiring baseline physiological data from the user via a wearable device. The wearable application 1220 may be configured as or otherwise support a means for determining a baseline stress level associated with the user based at least in part on the baseline physiological data, one or more user inputs received via a user device, or both. The wearable application 1220 may be configured as or otherwise support a means for determining, based at least in part on the baseline physiological data, a first baseline HRV value of the user during periods that the user is awake, and a second baseline HRV value of the user during periods that the user is asleep. The wearable application 1220 may be configured as or otherwise support a means for acquiring additional physiological data from the user via the wearable device throughout a time interval that spans a plurality of days and a plurality of nights. The wearable application 1220 may be configured as or otherwise support a means for determining, based at least in part on the additional physiological data, a first set of HRV values of the user during periods of the time interval that the user is awake, and a second set of HRV values of the user during periods of the time interval that the user is asleep. The wearable application 1220 may be configured as or otherwise support a means for determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both. The wearable application 1220 may be configured as or otherwise support a means for displaying, to the user via a GUI of the user device, a visual representation of the cumulative stress level.

Additionally, or alternatively, the wearable application 1220 may support measuring cumulative stress of a user over time in accordance with examples as disclosed herein. For example, the wearable application 1220 may be configured as or otherwise support a means for acquiring baseline physiological data from the user via a wearable device. The wearable application 1220 may be configured as or otherwise support a means for determining a baseline stress level associated with the user based at least in part on the baseline physiological data, one or more user inputs received via a user device, or both. The wearable application 1220 may be configured as or otherwise support a means for determining, based at least in part on the baseline physiological data, a first baseline HRV value of the user during periods that the user is awake, and a second baseline HRV value of the user during periods that the user is asleep. The wearable application 1220 may be configured as or otherwise support a means for acquiring additional physiological data from the user via the wearable device throughout a time interval that spans a plurality of days and a plurality of nights. The wearable application 1220 may be configured as or otherwise support a means for determining, based at least in part on the additional physiological data, a first set of HRV values of the user during periods of the time interval that the user is awake, and a second set of HRV values of the user during periods of the time interval that the user is asleep. The wearable application 1220 may be configured as or otherwise support a means for determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both. The wearable application 1220 may be configured as or otherwise support a means for display, to the user via a GUI of the user device, a visual representation of the cumulative stress level.

The wearable application 1220 may include an application (e.g., "app"), program, software, or other component which is configured to facilitate communications with a ring 104, server 110, other user devices 106, and the like. For example, the wearable application 1220 may include an application executable on a user device 106 which is configured to receive data (e.g., physiological data) from a ring 104, perform processing operations on the received data, transmit and receive data with the servers 110, and cause presentation of data to a user 102.

Figure 13:
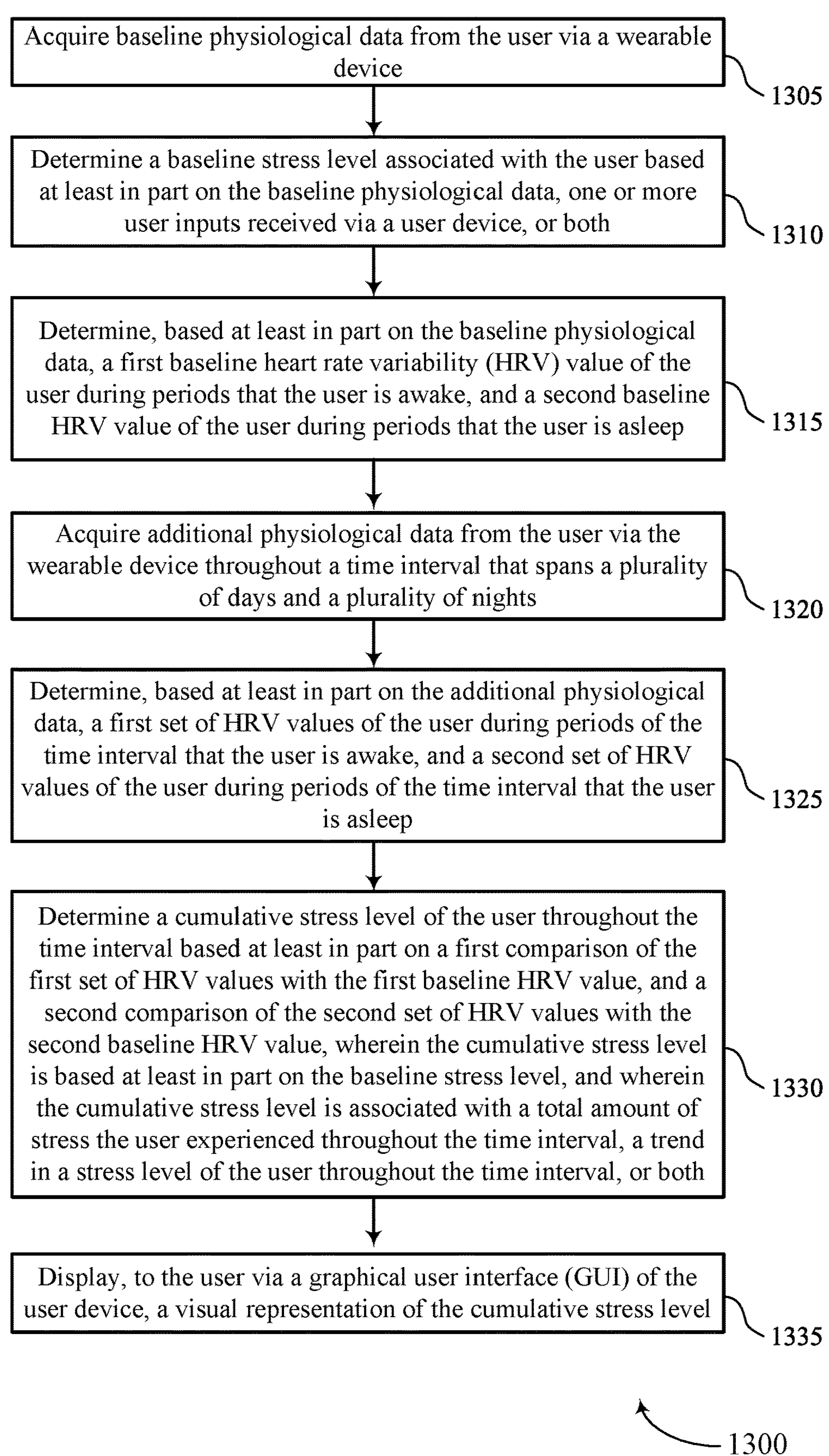
FIG. 13 shows a flowchart illustrating methods that support techniques for measuring cumulative stress using wearable-based data in accordance with aspects of the present disclosure.

FIG. 13 shows a flowchart illustrating a method 1300 that supports techniques for measuring cumulative stress using wearable-based data in accordance with aspects of the present disclosure. The operations of the method 1300 may be implemented by a user device or its components as described herein. For example, the operations of the method 1300 may be performed by a user device as described with reference to FIGS. 1 through 12. In some examples, a user device may execute a set of instructions to control the functional elements of the user device to perform the described functions. Additionally, or alternatively, the user device may perform aspects of the described functions using special-purpose hardware.

At 1305, the method may include acquiring baseline physiological data from the user via a wearable device. The operations of block 1305 may be performed in accordance with examples as disclosed herein. In some examples, aspects of the operations of 1305 may be performed by a data acquisition component 1125 as described with reference to FIG. 11.

At 1310, the method may include determining a baseline stress level associated with the user based at least in part on the baseline physiological data, one or more user inputs received via a user device, or both. The operations of block 1310 may be performed in accordance with examples as disclosed herein. In some examples, aspects of the operations of 1310 may be performed by a baseline stress level component 1130 as described with reference to FIG. 11.

At 1315, the method may include determining, based at least in part on the baseline physiological data, a first baseline HRV value of the user during periods that the user is awake, and a second baseline HRV value of the user during periods that the user is asleep. The operations of block 1315 may be performed in accordance with examples as disclosed herein. In some examples, aspects of the operations of 1315 may be performed by an HRV component 1135 as described with reference to FIG. 11.

At 1320, the method may include acquiring additional physiological data from the user via the wearable device throughout a time interval that spans a plurality of days and a plurality of nights. The operations of block 1320 may be performed in accordance with examples as disclosed herein. In some examples, aspects of the operations of 1320 may be performed by a data acquisition component 1125 as described with reference to FIG. 11.

At 1325, the method may include determining, based at least in part on the additional physiological data, a first set of HRV values of the user during periods of the time interval that the user is awake, and a second set of HRV values of the user during periods of the time interval that the user is asleep. The operations of block 1325 may be performed in accordance with examples as disclosed herein. In some examples, aspects of the operations of 1325 may be performed by an HRV component 1135 as described with reference to FIG. 11.

At 1330, the method may include determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both. The operations of block 1330 may be performed in accordance with examples as disclosed herein. In some examples, aspects of the operations of 1330 may be performed by a cumulative stress level component 1140 as described with reference to FIG. 11.

At 1335, the method may include displaying, to the user via a GUI of the user device, a visual representation of the cumulative stress level. The operations of block 1335 may be performed in accordance with examples as disclosed herein. In some examples, aspects of the operations of 1335 may be performed by a user interface component 1145 as described with reference to FIG. 11.

It should be noted that the methods described above describe possible implementations, and that the operations and the steps may be rearranged or otherwise modified and that other implementations are possible. Furthermore, aspects from two or more of the methods may be combined.

A method by an apparatus is described. The method may include acquiring baseline physiological data from the user via a wearable device, determining a baseline stress level associated with the user based at least in part on the baseline physiological data, one or more user inputs received via a user device, or both, determining, based at least in part on the baseline physiological data, a first baseline HRV value of the user during periods that the user is awake, and a second baseline HRV value of the user during periods that the user is asleep, acquiring additional physiological data from the user via the wearable device throughout a time interval that spans a plurality of days and a plurality of nights, determining, based at least in part on the additional physiological data, a first set of HRV values of the user during periods of the time interval that the user is awake, and a second set of HRV values of the user during periods of the time interval that the user is asleep, determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and displaying, to the user via a GUI of the user device, a visual representation of the cumulative stress level.

An apparatus is described. The apparatus may include one or more memories storing processor executable code, and one or more processors coupled with the one or more memories. The one or more processors may individually or collectively operable to execute the code to cause the apparatus to acquire baseline physiological data from the user via a wearable device, determine a baseline stress level associated with the user based at least in part on the baseline physiological data, one or more user inputs received via a user device, or both, determine, based at least in part on the baseline physiological data, a first baseline HRV value of the user during periods that the user is awake, and a second baseline HRV value of the user during periods that the user is asleep, acquire additional physiological data from the user via the wearable device throughout a time interval that spans a plurality of days and a plurality of nights, determine, based at least in part on the additional physiological data, a first set of HRV values of the user during periods of the time interval that the user is awake, and a second set of HRV values of the user during periods of the time interval that the user is asleep, determine a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and display, to the user via a GUI of the user device, a visual representation of the cumulative stress level.

Another apparatus is described. The apparatus may include means for acquiring baseline physiological data from the user via a wearable device, means for determining a baseline stress level associated with the user based at least in part on the baseline physiological data, one or more user inputs received via a user device, or both, means for determining, based at least in part on the baseline physiological data, a first baseline HRV value of the user during periods that the user is awake, and a second baseline HRV value of the user during periods that the user is asleep, means for acquiring additional physiological data from the user via the wearable device throughout a time interval that spans a plurality of days and a plurality of nights, means for determining, based at least in part on the additional physiological data, a first set of HRV values of the user during periods of the time interval that the user is awake, and a second set of HRV values of the user during periods of the time interval that the user is asleep, means for determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and means for displaying, to the user via a GUI of the user device, a visual representation of the cumulative stress level.

A non-transitory computer-readable medium storing code is described. The code may include instructions executable by a processor to acquire baseline physiological data from the user via a wearable device, determine a baseline stress level associated with the user based at least in part on the baseline physiological data, one or more user inputs received via a user device, or both, determine, based at least in part on the baseline physiological data, a first baseline HRV value of the user during periods that the user is awake, and a second baseline HRV value of the user during periods that the user is asleep, acquire additional physiological data from the user via the wearable device throughout a time interval that spans a plurality of days and a plurality of nights, determine, based at least in part on the additional physiological data, a first set of HRV values of the user during periods of the time interval that the user is awake, and a second set of HRV values of the user during periods of the time interval that the user is asleep, determine a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and display, to the user via a GUI of the user device, a visual representation of the cumulative stress level.

Some examples of the method, apparatuses, and non-transitory computer-readable medium described herein may further include operations, features, means, or instructions for determining one or more stress scores associated with the user throughout periods of the time interval that the user may be awake based at least in part on the first comparison of the first set of HRV values with the first baseline HRV value and determining one or more recovery scores associated with the user throughout periods of the time interval that the user may be asleep based at least in part on the second comparison of the second set of HRV values with the second baseline HRV value, wherein the cumulative stress level may be based at least in part on the one or more stress scores and the one or more recovery scores.

Some examples of the method, apparatuses, and non-transitory computer-readable medium described herein may further include operations, features, means, or instructions for determining the baseline stress level associated with the user based at least in part on the baseline physiological data, wherein the baseline physiological data comprises heart rate data, respiratory rate data, skin temperature data, or any combination thereof, and wherein determining the cumulative stress level may be based at least in part on the baseline stress level.

Some examples of the method, apparatuses, and non-transitory computer-readable medium described herein may further include operations, features, means, or instructions for predicting a burnout condition of the user, a chronic stress condition of the user, or both, based at least in part on a comparison between the cumulative stress level and the baseline stress level associated with the user and causing the GUI of the user device to display an alert associated with the burnout condition, the chronic stress condition, or both.

Some examples of the method, apparatuses, and non-transitory computer-readable medium described herein may further include operations, features, means, or instructions for receiving, from the user device, the one or more user inputs comprising one or more characteristics associated with the user, wherein determining the baseline stress level may be based at least in part on the user input.

Some examples of the method, apparatuses, and non-transitory computer-readable medium described herein may further include operations, features, means, or instructions for acquiring additional baseline physiological data associated with a plurality of users associated with a set of characteristics that may be common between the plurality of users and the user and determining a plurality of baseline stress levels associated with the plurality of users, wherein determining the baseline stress level associated with the user may be based at least in part on determining the plurality of baseline stress levels and a comparison between the baseline physiological data associated with the user and the additional baseline physiological data associated with the plurality of users.

In some examples of the method, apparatuses, and non-transitory computer-readable medium described herein, acquiring the baseline physiological data may include operations, features, means, or instructions for providing, to the user via the GUI of the user device, instructions for the user to modify one or more behaviors associated with a target stress level of the user, receiving, from the wearable device and based at least in part on providing the instructions to the user, a plurality of physiological measurements associated with the one or more behaviors, and determining the baseline stress level associated with the user based at least in part on comparing the plurality of physiological measurements with the baseline physiological data, wherein determining the cumulative stress level may be based at least in part on determining the baseline stress level.

In some examples of the method, apparatuses, and non-transitory computer-readable medium described herein, the visual representation indicates a relative change between a baseline stress level associated with the user and the cumulative stress level.

Some examples of the method, apparatuses, and non-transitory computer-readable medium described herein may further include operations, features, means, or instructions for classifying a plurality of periods within time interval that the user may be either awake or asleep as one of a stressful period, a recovery period, or a neutral period based at least in part on the comparison of the first set of HRV values with the first baseline HRV value and the comparison of the second set of HRV values with the second baseline HRV value, wherein determining the cumulative stress level may be based at least in part on the classifying.

In some examples of the method, apparatuses, and non-transitory computer-readable medium described herein, providing, via the GUI of the user device, feedback to the user comprising instructions for modifying one or more behaviors of the user, the one or more behaviors configured to modify the cumulative stress level of the user.

In some examples of the method, apparatuses, and non-transitory computer-readable medium described herein, the baseline physiological data may be acquired throughout a second time interval prior to the time interval, the second time interval comprising a second plurality of days and a second plurality of nights.

In some examples of the method, apparatuses, and non-transitory computer-readable medium described herein, the wearable device comprises a wearable ring device.

A method for measuring cumulative stress of a user over time by an apparatus is described. The method may include acquiring baseline physiological data from the user via a wearable device, determining a baseline stress level associated with the user based at least in part on the baseline physiological data, one or more user inputs received via a user device, or both, determining, based at least in part on the baseline physiological data, a first baseline HRV value of the user during periods that the user is awake, and a second baseline HRV value of the user during periods that the user is asleep, acquiring additional physiological data from the user via the wearable device throughout a time interval that spans a plurality of days and a plurality of nights, determining, based at least in part on the additional physiological data, a first set of HRV values of the user during periods of the time interval that the user is awake, and a second set of HRV values of the user during periods of the time interval that the user is asleep, determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and display, to the user via a GUI of the user device, a visual representation of the cumulative stress level.

An apparatus for measuring cumulative stress of a user over time is described. The apparatus may include one or more memories storing processor executable code, and one or more processors coupled with the one or more memories. The one or more processors may individually or collectively operable to execute the code to cause the apparatus to acquire baseline physiological data from the user via a wearable device, determine a baseline stress level associated with the user based at least in part on the baseline physiological data, one or more user inputs received via a user device, or both, determine, based at least in part on the baseline physiological data, a first baseline HRV value of the user during periods that the user is awake, and a second baseline HRV value of the user during periods that the user is asleep, acquire additional physiological data from the user via the wearable device throughout a time interval that spans a plurality of days and a plurality of nights, determine, based at least in part on the additional physiological data, a first set of HRV values of the user during periods of the time interval that the user is awake, and a second set of HRV values of the user during periods of the time interval that the user is asleep, determine a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and display, to the user via a GUI of the user device, a visual representation of the cumulative stress level.

Another apparatus for measuring cumulative stress of a user over time is described. The apparatus may include means for acquiring baseline physiological data from the user via a wearable device, means for determining a baseline stress level associated with the user based at least in part on the baseline physiological data, one or more user inputs received via a user device, or both, means for determining, based at least in part on the baseline physiological data, a first baseline HRV value of the user during periods that the user is awake, and a second baseline HRV value of the user during periods that the user is asleep, means for acquiring additional physiological data from the user via the wearable device throughout a time interval that spans a plurality of days and a plurality of nights, means for determining, based at least in part on the additional physiological data, a first set of HRV values of the user during periods of the time interval that the user is awake, and a second set of HRV values of the user during periods of the time interval that the user is asleep, means for determining a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and means for display, to the user via a GUI of the user device, a visual representation of the cumulative stress level.

A non-transitory computer-readable medium storing code for measuring cumulative stress of a user over time is described. The code may include instructions executable by a processor to acquire baseline physiological data from the user via a wearable device, determine a baseline stress level associated with the user based at least in part on the baseline physiological data, one or more user inputs received via a user device, or both, determine, based at least in part on the baseline physiological data, a first baseline HRV value of the user during periods that the user is awake, and a second baseline HRV value of the user during periods that the user is asleep, acquire additional physiological data from the user via the wearable device throughout a time interval that spans a plurality of days and a plurality of nights, determine, based at least in part on the additional physiological data, a first set of HRV values of the user during periods of the time interval that the user is awake, and a second set of HRV values of the user during periods of the time interval that the user is asleep, determine a cumulative stress level of the user throughout the time interval based at least in part on a first comparison of the first set of HRV values with the first baseline HRV value, and a second comparison of the second set of HRV values with the second baseline HRV value, wherein the cumulative stress level is based at least in part on the baseline stress level, and wherein the cumulative stress level is associated with a total amount of stress the user experienced throughout the time interval, a trend in a stress level of the user throughout the time interval, or both, and display, to the user via a GUI of the user device, a visual representation of the cumulative stress level.

A method for measuring acute stress of a user by an apparatus is described. The method may include acquiring physiological data from the user via a wearable device throughout a time interval, the physiological data comprising at least heart rate data and motion data, determining that the user is awake and that the user is sedentary throughout the time interval based at least in part on the heart rate data satisfying a heart rate threshold value and the motion data satisfying a motion threshold value, determining a daytime HRV value of the user for the time interval based at least in part on determining that the user was sedentary and awake throughout the time interval, comparing the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, determining an acute stress level of the user during the time interval based at least in part on comparing the daytime HRV value with the baseline daytime HRV data, the acute stress level associated with a relative amount of stress experienced by the user throughout the time interval, and displaying, to the user via a GUI of a user device, a visual representation of the acute stress level.

An apparatus for measuring acute stress of a user is described. The apparatus may include one or more memories storing processor executable code, and one or more processors coupled with the one or more memories. The one or more processors may individually or collectively operable to execute the code to cause the apparatus to acquire physiological data from the user via a wearable device throughout a time interval, the physiological data comprising at least heart rate data and motion data, determine that the user is awake and that the user is sedentary throughout the time interval based at least in part on the heart rate data satisfying a heart rate threshold value and the motion data satisfying a motion threshold value, determine a daytime HRV value of the user for the time interval based at least in part on determining that the user was sedentary and awake throughout the time interval, compare the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, determine an acute stress level of the user during the time interval based at least in part on comparing the daytime HRV value with the baseline daytime HRV data, the acute stress level associated with a relative amount of stress experienced by the user throughout the time interval, and display, to the user via a GUI of a user device, a visual representation of the acute stress level.

Another apparatus for measuring acute stress of a user is described. The apparatus may include means for acquiring physiological data from the user via a wearable device throughout a time interval, the physiological data comprising at least heart rate data and motion data, means for determining that the user is awake and that the user is sedentary throughout the time interval based at least in part on the heart rate data satisfying a heart rate threshold value and the motion data satisfying a motion threshold value, means for determining a daytime HRV value of the user for the time interval based at least in part on determining that the user was sedentary and awake throughout the time interval, means for comparing the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, means for determining an acute stress level of the user during the time interval based at least in part on comparing the daytime HRV value with the baseline daytime HRV data, the acute stress level associated with a relative amount of stress experienced by the user throughout the time interval, and means for displaying, to the user via a GUI of a user device, a visual representation of the acute stress level.

A non-transitory computer-readable medium storing code for measuring acute stress of a user is described. The code may include instructions executable by a processor to acquire physiological data from the user via a wearable device throughout a time interval, the physiological data comprising at least heart rate data and motion data, determine that the user is awake and that the user is sedentary throughout the time interval based at least in part on the heart rate data satisfying a heart rate threshold value and the motion data satisfying a motion threshold value, determine a daytime HRV value of the user for the time interval based at least in part on determining that the user was sedentary and awake throughout the time interval, compare the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, determine an acute stress level of the user during the time interval based at least in part on comparing the daytime HRV value with the baseline daytime HRV data, the acute stress level associated with a relative amount of stress experienced by the user throughout the time interval, and display, to the user via a GUI of a user device, a visual representation of the acute stress level.

Some examples of the method, apparatuses, and non-transitory computer-readable medium described herein may further include operations, features, means, or instructions for determining an expected daytime HRV variance associated with the user based at least in part on baseline night time HRV data acquired from the user while the user may be sleeping and determining the acute stress level based at least in part on comparing a difference between the daytime HRV value and the baseline daytime HRV data with the expected daytime HRV variance.

Some examples of the method, apparatuses, and non-transitory computer-readable medium described herein may further include operations, features, means, or instructions for determining the expected daytime HRV variance associated with the user based at least in part a plurality of daytime HRV values for a plurality of users, the plurality of users associated with a set of characteristics that may be common between the plurality of users and the user.

Some examples of the method, apparatuses, and non-transitory computer-readable medium described herein may further include operations, features, means, or instructions for determining that the heart rate data satisfies one or more measurement quality criteria, wherein determining the daytime HRV value may be based at least in part on the heart rate data satisfying the one or more measurement quality criteria.

Some examples of the method, apparatuses, and non-transitory computer-readable medium described herein may further include operations, features, means, or instructions for determining that the heart rate data fails to satisfy one or more measurement quality criteria, normalizing the heart rate data, skin temperature data, or both, acquired from the user via the wearable device, inputting the normalized heart rate data, the normalized skin temperature data, or both, into a machine learning model, and obtaining an imputed daytime HRV value as an output of the machine learning model based at least in part on inputting the normalized heart rate data, the normalized skin temperature data, or both, into the machine learning model, the imputed daytime HRV value comprising the daytime HRV value that may be compared to the baseline daytime HRV data.

Some examples of the method, apparatuses, and non-transitory computer-readable medium described herein may further include operations, features, means, or instructions for scaling the normalized heart rate data, the normalized skin temperature data, or both, based at least in part on baseline heart rate data and baseline skin temperature data associated with the user, respectively, wherein inputting the normalized heart rate data, the normalized skin temperature data, or both, may be based at least in part on the scaling.

Some examples of the method, apparatuses, and non-transitory computer-readable medium described herein may further include operations, features, means, or instructions for inputting the motion data into the machine learning model, wherein obtaining the imputed daytime HRV value from the machine learning model may be based at least in part on inputting the motion data into the machine learning model.

Some examples of the method, apparatuses, and non-transitory computer-readable medium described herein may further include operations, features, means, or instructions for inputting the baseline daytime HRV data, baseline heart rate data corresponding to the baseline daytime HRV data, baseline skin temperature data corresponding to the baseline daytime HRV data, or any combination thereof, into the machine learning model and training the machine learning model to generate imputed daytime HRV values associated with the user based at least in part on inputting the baseline daytime HRV data, the baseline heart rate data, the baseline skin temperature data, or any combination thereof, wherein obtaining the imputed daytime HRV value may be based at least in part on training the machine learning model.

Some examples of the method, apparatuses, and non-transitory computer-readable medium described herein may further include operations, features, means, or instructions for classifying the time interval as one of a stressful period, a recovery period, or a neutral period based at least in part on the acute stress level satisfying a stress threshold metric, a recovery threshold metric, or both, wherein displaying the visual representation of the acute stress level may be based at least in part on the classifying.

In some examples of the method, apparatuses, and non-transitory computer-readable medium described herein, providing, via the GUI of the user device, feedback to the user comprising instructions for modifying one or more behaviors of the user, the one or more behaviors corresponding to the acute stress level of the user.

Some examples of the method, apparatuses, and non-transitory computer-readable medium described herein may further include operations, features, means, or instructions for determining a second daytime HRV value of the user based at least in part on acquiring second physiological data throughout a second time interval, comparing the second daytime HRV value to the baseline daytime HRV data, determining a second acute stress level of the user during the second time interval based at least in part on comparing the second daytime HRV value with the baseline daytime HRV data, and displaying, to the user via the GUI of the user device, a second visual representation of the second acute stress level.

In some examples of the method, apparatuses, and non-transitory computer-readable medium described herein, the second visual representation indicates a relative change between the acute stress level associated with the time interval and the second acute stress level associated with the second time interval.

In some examples of the method, apparatuses, and non-transitory computer-readable medium described herein, the time interval comprises a plurality of seconds, minutes, or hours within a day.

In some examples of the method, apparatuses, and non-transitory computer-readable medium described herein, the wearable device comprises a wearable ring device.

A method for measuring acute stress of a user by an apparatus is described. The method may include acquiring physiological data from the user via a wearable device throughout a time interval, the physiological data comprising at least heart rate data and motion data, determining that the user is awake and that the user is sedentary throughout the time interval based at least in part on the heart rate data and the motion data, determining a daytime HRV value of the user for the time interval based at least in part on determining that the user is sedentary and awake throughout the time interval, comparing the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, determining an acute stress level of the user during the time interval based at least in part on comparing the daytime HRV value with the baseline daytime HRV data, the acute stress level associated with a relative amount of stress experienced by the user throughout the time interval, and display, to the user via a GUI of a user device, a visual representation of the acute stress level.

An apparatus for measuring acute stress of a user is described. The apparatus may include one or more memories storing processor executable code, and one or more processors coupled with the one or more memories. The one or more processors may individually or collectively operable to execute the code to cause the apparatus to acquire physiological data from the user via a wearable device throughout a time interval, the physiological data comprising at least heart rate data and motion data, determine that the user is awake and that the user is sedentary throughout the time interval based at least in part on the heart rate data and the motion data, determine a daytime HRV value of the user for the time interval based at least in part on determining that the user is sedentary and awake throughout the time interval, compare the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, determine an acute stress level of the user during the time interval based at least in part on comparing the daytime HRV value with the baseline daytime HRV data, the acute stress level associated with a relative amount of stress experienced by the user throughout the time interval, and display, to the user via a GUI of a user device, a visual representation of the acute stress level.

Another apparatus for measuring acute stress of a user is described. The apparatus may include means for acquiring physiological data from the user via a wearable device throughout a time interval, the physiological data comprising at least heart rate data and motion data, means for determining that the user is awake and that the user is sedentary throughout the time interval based at least in part on the heart rate data and the motion data, means for determining a daytime HRV value of the user for the time interval based at least in part on determining that the user is sedentary and awake throughout the time interval, means for comparing the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, means for determining an acute stress level of the user during the time interval based at least in part on comparing the daytime HRV value with the baseline daytime HRV data, the acute stress level associated with a relative amount of stress experienced by the user throughout the time interval, and means for display, to the user via a GUI of a user device, a visual representation of the acute stress level.

A non-transitory computer-readable medium storing code for measuring acute stress of a user is described. The code may include instructions executable by a processor to acquire physiological data from the user via a wearable device throughout a time interval, the physiological data comprising at least heart rate data and motion data, determine that the user is awake and that the user is sedentary throughout the time interval based at least in part on the heart rate data and the motion data, determine a daytime HRV value of the user for the time interval based at least in part on determining that the user is sedentary and awake throughout the time interval, compare the daytime HRV value of the user to baseline daytime HRV data associated with the user, the baseline daytime HRV data determined based on additional physiological data acquired from the user throughout a reference time interval comprising a plurality of days prior to the time interval, wherein the baseline daytime HRV data is collected during periods of the reference time interval that the user was awake and sedentary, determine an acute stress level of the user during the time interval based at least in part on comparing the daytime HRV value with the baseline daytime HRV data, the acute stress level associated with a relative amount of stress experienced by the user throughout the time interval, and display, to the user via a GUI of a user device, a visual representation of the acute stress level.

A method by an apparatus is described. The method may include acquiring physiological data from a user via wearable device throughout a plurality of time intervals, wherein each time interval comprises an awake interval that the user is awake and an asleep interval that that the user is asleep, the physiological data comprising at least HRV data, determining, for the plurality of time intervals and based at least in part on the HRV data, a stress index and a recovery index associated with the awake interval of a respective time interval, and a sleep recovery index associated with the asleep interval of the respective time interval, determining a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and displaying, to the user via a GUI of a user device, a visual representation of the stress resilience metric.

An apparatus is described. The apparatus may include one or more memories storing processor executable code, and one or more processors coupled with the one or more memories. The one or more processors may individually or collectively operable to execute the code to cause the apparatus to acquire physiological data from a user via wearable device throughout a plurality of time intervals, wherein each time interval comprises an awake interval that the user is awake and an asleep interval that that the user is asleep, the physiological data comprising at least HRV data, determine, for the plurality of time intervals and based at least in part on the HRV data, a stress index and a recovery index associated with the awake interval of a respective time interval, and a sleep recovery index associated with the asleep interval of the respective time interval, determine a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and display, to the user via a GUI of a user device, a visual representation of the stress resilience metric.

Another apparatus is described. The apparatus may include means for acquiring physiological data from a user via wearable device throughout a plurality of time intervals, wherein each time interval comprises an awake interval that the user is awake and an asleep interval that that the user is asleep, the physiological data comprising at least HRV data, means for determining, for the plurality of time intervals and based at least in part on the HRV data, a stress index and a recovery index associated with the awake interval of a respective time interval, and a sleep recovery index associated with the asleep interval of the respective time interval, means for determining a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and means for displaying, to the user via a GUI of a user device, a visual representation of the stress resilience metric.

A non-transitory computer-readable medium storing code is described. The code may include instructions executable by a processor to acquire physiological data from a user via wearable device throughout a plurality of time intervals, wherein each time interval comprises an awake interval that the user is awake and an asleep interval that that the user is asleep, the physiological data comprising at least HRV data, determine, for the plurality of time intervals and based at least in part on the HRV data, a stress index and a recovery index associated with the awake interval of a respective time interval, and a sleep recovery index associated with the asleep interval of the respective time interval, determine a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and display, to the user via a GUI of a user device, a visual representation of the stress resilience metric.

In some examples of the method, apparatuses, and non-transitory computer-readable medium described herein, the plurality of time intervals comprises a second time interval including a first awake interval and a first asleep interval subsequent to the first awake interval and the method, apparatuses, and non-transitory computer-readable medium may include further operations, features, means, or instructions for determining an absence of physiological data collected during either the first awake interval or the first asleep interval and refraining from determining a stress index, a recovery index, and a sleep recovery index corresponding to the first time interval based at least in part on the absence of physiological data collected during either the first awake interval or the first asleep interval.

In some examples of the method, apparatuses, and non-transitory computer-readable medium described herein, wherein the stress index and the recovery index associated with the awake interval of the respective time interval may be based at least in part on a comparison of a first portion of the HRV data collected during the awake interval with baseline daytime HRV data associated with the user during periods that the user may be awake and wherein the sleep recovery index associated with the asleep interval of the respective time interval may be based at least in part on a comparison of a second portion of the HRV data collected during the asleep interval with baseline nighttime HRV data associated with the user during periods that the user may be asleep.

In some examples of the method, apparatuses, and non-transitory computer-readable medium described herein, the sleep recovery index of the respective time interval may be determined based at least in part on a weighted average of a duration of the asleep interval of the respective time interval, a quality of sleep of the user during the asleep interval of the respective time interval, a resting heart rate of the user throughout the asleep interval of the respective time interval, and an HRV variance of the HRV data collected during the asleep interval of the respective time interval.

Some examples of the method, apparatuses, and non-transitory computer-readable medium described herein may further include operations, features, means, or instructions for classifying each time interval of the plurality of time intervals with a stress resilience level based at least in part on comparing the stress index, the recovery index, and the sleep recovery index corresponding to the respective time interval, wherein displaying the visual representation of the stress resilience metric may be based at least in part on the classifying.

Some examples of the method, apparatuses, and non-transitory computer-readable medium described herein may further include operations, features, means, or instructions for displaying, to the user via the GUI of a user device, a plurality of stress resilience metrics corresponding to the plurality of time intervals based at least in part on the classifying.

Some examples of the method, apparatuses, and non-transitory computer-readable medium described herein may further include operations, features, means, or instructions for displaying, to the user via the GUI of a user device, an indication of the stress index, the recovery index, and the sleep recovery index corresponding to the time interval of the plurality of time intervals.

Some examples of the method, apparatuses, and non-transitory computer-readable medium described herein may further include operations, features, means, or instructions for displaying, to the user via the GUI of a user device and based at least in part on determining the stress resilience metric, feedback to the user comprising instructions for maintaining one or more first behaviors of the user, modifying one or more second behaviors of the user, or both, wherein the instructions may be configured to modify or maintain the stress resilience metric.

In some examples of the method, apparatuses, and non-transitory computer-readable medium described herein, the physiological data comprises heart rate data, respiratory rate data, skin temperature data, or any combination thereof.

In some examples of the method, apparatuses, and non-transitory computer-readable medium described herein, the plurality of time intervals comprises a first time interval and a second time interval that may be more recent than the first time interval, the weighted sum comprises a first weight associated with the first time interval and a second weight associated with the second time interval, and the second weight may be greater than the first weight based at least in part on the second time interval being more recent than the first time interval.

In some examples of the method, apparatuses, and non-transitory computer-readable medium described herein, the wearable device comprises a wearable ring device.

A method for determining a user's resilience to stress by an apparatus is described. The method may include acquiring physiological data from a user via wearable device throughout a plurality of time intervals, wherein each time interval comprises an awake interval that the user is awake and an asleep interval that that the user is asleep, the physiological data comprising at least HRV data, determining, for the plurality of time intervals and based at least in part on the HRV data, a stress index and a recovery index associated with the awake interval of a respective time interval, and a sleep recovery index associated with the asleep interval of the respective time interval, determining a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and display, to the user via a GUI of a user device, a visual representation of the stress resilience metric.

An apparatus for determining a user's resilience to stress is described. The apparatus may include one or more memories storing processor executable code, and one or more processors coupled with the one or more memories. The one or more processors may individually or collectively operable to execute the code to cause the apparatus to acquire physiological data from a user via wearable device throughout a plurality of time intervals, wherein each time interval comprises an awake interval that the user is awake and an asleep interval that that the user is asleep, the physiological data comprising at least HRV data, determine, for the plurality of time intervals and based at least in part on the HRV data, a stress index and a recovery index associated with the awake interval of a respective time interval, and a sleep recovery index associated with the asleep interval of the respective time interval, determine a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and display, to the user via a GUI of a user device, a visual representation of the stress resilience metric.

Another apparatus for determining a user's resilience to stress is described. The apparatus may include means for acquiring physiological data from a user via wearable device throughout a plurality of time intervals, wherein each time interval comprises an awake interval that the user is awake and an asleep interval that that the user is asleep, the physiological data comprising at least HRV data, means for determining, for the plurality of time intervals and based at least in part on the HRV data, a stress index and a recovery index associated with the awake interval of a respective time interval, and a sleep recovery index associated with the asleep interval of the respective time interval, means for determining a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and means for display, to the user via a GUI of a user device, a visual representation of the stress resilience metric.

A non-transitory computer-readable medium storing code for determining a user's resilience to stress is described. The code may include instructions executable by a processor to acquire physiological data from a user via wearable device throughout a plurality of time intervals, wherein each time interval comprises an awake interval that the user is awake and an asleep interval that that the user is asleep, the physiological data comprising at least HRV data, determine, for the plurality of time intervals and based at least in part on the HRV data, a stress index and a recovery index associated with the awake interval of a respective time interval, and a sleep recovery index associated with the asleep interval of the respective time interval, determine a stress resilience metric of the user based at least in part on a weighted sum of the stress indices, recovery indices, and sleep recovery indices of the plurality of time intervals, wherein the weighted sum is associated with a recency of the respective stress indices, recovery indices, and sleep recovery indices, wherein the stress resilience metric indicates a relative capability of the user to cope with stress, to recover from stress, or both, and display, to the user via a GUI of a user device, a visual representation of the stress resilience metric.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for measuring cumulative stress of a user over time, comprising:

acquiring baseline physiological data from the user via a wearable device, the baseline physiological data comprising at least a pulse waveform associated with a heart rate of the user;

determining a baseline stress level associated with the user based at least in part on the baseline physiological data, one or more user inputs received via a user device, or both;

determining, based at least in part on variation in an interbeat interval (IBI) of the pulse waveform of the baseline physiological data, a first baseline heart rate variability (HRV) value of the user during periods that the user is awake, and a second baseline HRV value of the user during periods that the user is asleep;

acquiring additional physiological data from the user via the wearable device throughout a time interval that spans a plurality of days and a plurality of nights;

determining, based at least in part on the additional physiological data, a first set of HRV values of the user during periods of the time interval that the user is awake, and a second set of HRV values of the user during periods of the time interval that the user is asleep;

determining one or more stress scores associated with the user throughout periods of the time interval that the user is awake based at least in part on a first comparison of the first set of HRV values with the first baseline HRV value;

determining one or more recovery scores associated with the user throughout periods of the time interval that the user is asleep based at least in part on a second comparison of the second set of HRV values with the second baseline HRV value;

determining a cumulative stress level of the user throughout the time interval based at least in part on the one or more stress scores associated with periods of the time interval that the user is awake, and the one or more recovery scores associated with periods of the time interval that the user is asleep, wherein the cumulative stress level is based at least in part on the baseline stress level, and wherein the cumulative stress level is associated with a total amount of stress the user experienced throughout the time interval, a trend in a stress level of the user throughout the time interval, or both; and displaying, to the user via a graphical user interface (GUI) of the user device, a visual representation of the cumulative stress level.

2. The method of claim 1, further comprising:

determining the baseline stress level associated with the user based at least in part on the baseline physiological data, wherein the baseline physiological data comprises heart rate data, respiratory rate data, skin temperature data, or any combination thereof, and wherein determining the cumulative stress level is based at least in part on the baseline stress level.

3. The method of claim 2, further comprising:

predicting a burnout condition of the user, a chronic stress condition of the user, or both, based at least in part on a comparison between the cumulative stress level and the baseline stress level associated with the user; and causing the GUI of the user device to display an alert associated with the burnout condition, the chronic stress condition, or both.

4. The method of claim 2, further comprising:

receiving, from the user device, the one or more user inputs comprising one or more characteristics associated with the user, wherein determining the baseline stress level is based at least in part on the one or more user inputs.

5. The method of claim 4, further comprising:

acquiring additional baseline physiological data associated with a plurality of users associated with a set of characteristics that are common between the plurality of users and the user; and determining a plurality of baseline stress levels associated with the plurality of users, wherein determining the baseline stress level associated with the user is based at least in part on determining the plurality of baseline stress levels and a comparison between the baseline physiological data associated with the user and the additional baseline physiological data associated with the plurality of users.

6. The method of claim 1, wherein acquiring the baseline physiological data further comprises:

providing, to the user via the GUI of the user device, instructions for the user to modify one or more behaviors associated with a target stress level of the user;

receiving, from the wearable device and based at least in part on providing the instructions to the user, a plurality of physiological measurements associated with the one or more behaviors; and determining the baseline stress level associated with the user based at least in part on comparing the plurality of physiological measurements with the baseline physiological data, wherein determining the cumulative stress level is based at least in part on determining the baseline stress level.

7. The method of claim 1, wherein the visual representation indicates a relative change between a baseline stress level associated with the user and the cumulative stress level.

8. The method of claim 1, further comprising:

classifying a plurality of periods within time interval that the user is either awake or asleep as one of a stressful period, a recovery period, or a neutral period based at least in part on the first comparison of the first set of HRV values with the first baseline HRV value and the second comparison of the second set of HRV values with the second baseline HRV value, wherein determining the cumulative stress level is based at least in part on the classifying.

9. The method of claim 1, further comprising:

providing, via the GUI of the user device, feedback to the user comprising instructions for modifying one or more behaviors of the user, the one or more behaviors configured to modify the cumulative stress level of the user.

10. The method of claim 1, wherein the baseline physiological data is acquired throughout a second time interval prior to the time interval, the second time interval comprising a second plurality of days and a second plurality of nights.

11. The method of claim 1, wherein the wearable device comprises a wearable ring device.

12. A system for measuring cumulative stress of a user over time, comprising:
- at least one processor;
- at least one memory coupled with the at least one processor; and
- instructions stored in the at least one memory and executable by the at least one processor to:
  - acquire baseline physiological data from the user via a wearable device, the baseline physiological data comprising at least a pulse waveform associated with a heart rate of the user;
  - determine a baseline stress level associated with the user based at least in part on the baseline physiological data, one or more user inputs received via a user device, or both;
  - determine, based at least in part on variation in an interbeat interval (IBI) of the pulse waveform of the baseline physiological data, a first baseline heart rate variability (HRV) value of the user during periods that the user is awake, and a second baseline HRV value of the user during periods that the user is asleep;
  - acquire additional physiological data from the user via the wearable device throughout a time interval that spans a plurality of days and a plurality of nights;
  - determine, based at least in part on the additional physiological data, a first set of HRV values of the user during periods of the time interval that the user is awake, and a second set of HRV values of the user during periods of the time interval that the user is asleep;
  - determine one or more stress scores associated with the user throughout periods of the time interval that the user is awake based at least in part on a first comparison of the first set of HRV values with the first baseline HRV value;
  - determine one or more recovery scores associated with the user throughout periods of the time interval that the user is asleep based at least in part on a second comparison of the second set of HRV values with the second baseline HRV value;
  - determine a cumulative stress level of the user throughout the time interval based at least in part on the one or more stress scores associated with periods of the time interval that the user is awake, and the one or more recovery scores associated with periods of the time interval that the user is asleep, wherein the cumulative stress level is based at least in part on the baseline stress level, and wherein the cumulative stress level is associated with a total amount of stress the user experienced throughout the time interval, a trend in a stress level of the user throughout the time interval, or both; and
  - display, to the user via a graphical user interface (GUI) of the user device, a visual representation of the cumulative stress level.

13. The system of claim 12, wherein the at least one processor is further configured to:
- determine the baseline stress level associated with the user based at least in part on the baseline physiological data, wherein the baseline physiological data comprises heart rate data, respiratory rate data, skin temperature data, or any combination thereof, and wherein determining the cumulative stress level is based at least in part on the baseline stress level.

14. The system of claim 13, wherein the at least one processor is further configured to:
- predict a burnout condition of the user, a chronic stress condition of the user, or both, based at least in part on a comparison between the cumulative stress level and the baseline stress level associated with the user; and
- cause the GUI of the user device to display an alert associated with the burnout condition, the chronic stress condition, or both.

15. The system of claim 12, wherein the at least one processor is further configured to:
- classify a plurality of periods within time interval that the user is either awake or asleep as one of a stressful period, a recovery period, or a neutral period based at least in part on the first comparison of the first set of HRV values with the first baseline HRV value and the second comparison of the second set of HRV values with the second baseline HRV value, wherein determining the cumulative stress level is based at least in part on the classifying.

16. A non-transitory computer-readable medium storing code for measuring cumulative stress of a user over time, the code comprising instructions executable by at least one processor to:
- acquire baseline physiological data from the user via a wearable device, the baseline physiological data comprising at least a pulse waveform associated with a heart rate of the user;
- determine a baseline stress level associated with the user based at least in part on the baseline physiological data, one or more user inputs received via a user device, or both;
- determine, based at least in part on variation in an interbeat interval (IBI) of the pulse waveform of the baseline physiological data, a first baseline heart rate variability (HRV) value of the user during periods that the user is awake, and a second baseline HRV value of the user during periods that the user is asleep;
- acquire additional physiological data from the user via the wearable device throughout a time interval that spans a plurality of days and a plurality of nights;
- determine, based at least in part on the additional physiological data, a first set of HRV values of the user during periods of the time interval that the user is awake, and a second set of HRV values of the user during periods of the time interval that the user is asleep;
- determine one or more stress scores associated with the user throughout periods of the time interval that the user is awake based at least in part on a first comparison of the first set of HRV values with the first baseline HRV value;
- determine one or more recovery scores associated with the user throughout periods of the time interval that the user is asleep based at least in part on a second comparison of the second set of HRV values with the second baseline HRV value;
- determine a cumulative stress level of the user throughout the time interval based at least in part on the one or more stress scores associated with periods of the time interval that the user is awake, and the one or more recovery scores associated with periods of the time interval that the user is asleep, wherein the cumulative stress level is based at least in part on the baseline stress level, and wherein the cumulative stress level is associated with a total amount of stress the user experienced throughout the time interval, a trend in a stress level of the user throughout the time interval, or both; and display, to the user via a graphical user interface (GUI) of the user device, a visual representation of the cumulative stress level.

17. The non-transitory computer-readable medium of claim 16, the code comprising instructions executable by the at least one processor to:

determine the baseline stress level associated with the user based at least in part on the baseline physiological data, wherein the baseline physiological data comprises heart rate data, respiratory rate data, skin temperature data, or any combination thereof, and wherein determining the cumulative stress level is based at least in part on the baseline stress level.

18. The non-transitory computer-readable medium of claim 17, the code comprising instructions executable by the at least one processor to:

predict a burnout condition of the user, a chronic stress condition of the user, or both, based at least in part on a comparison between the cumulative stress level and the baseline stress level associated with the user; and cause the GUI of the user device to display an alert associated with the burnout condition, the chronic stress condition, or both.

19. The non-transitory computer-readable medium of claim 16, the code comprising instructions executable by the at least one processor to:

classify a plurality of periods within time interval that the user is either awake or asleep as one of a stressful period, a recovery period, or a neutral period based at least in part on the first comparison of the first set of HRV values with the first baseline HRV value and the second comparison of the second set of HRV values with the second baseline HRV value, wherein determining the cumulative stress level is based at least in part on the classifying.

* * * * *